United States Patent
Pugia

(10) Patent No.: US 9,291,629 B2
(45) Date of Patent: Mar. 22, 2016

(54) ADIPONECTIN RECEPTOR C-TERMINAL FRAGMENTS (CTF)-IMMUNOGLOBULIN

(75) Inventor: Michael Pugia, Granger, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/111,506

(22) PCT Filed: Feb. 22, 2012

(86) PCT No.: PCT/US2012/026141
§ 371 (c)(1),
(2), (4) Date: Oct. 11, 2013

(87) PCT Pub. No.: WO2012/141792
PCT Pub. Date: Oct. 18, 2012

(65) Prior Publication Data
US 2014/0038890 A1    Feb. 6, 2014

Related U.S. Application Data

(60) Provisional application No. 61/445,103, filed on Apr. 11, 2011.

(51) Int. Cl.
*G01N 33/53* (2006.01)
*G01N 33/68* (2006.01)
*G01N 33/574* (2006.01)
*G01N 33/74* (2006.01)

(52) U.S. Cl.
CPC .......... *G01N 33/6854* (2013.01); *G01N 33/574* (2013.01); *G01N 33/6857* (2013.01); *G01N 33/74* (2013.01); *G01N 2800/042* (2013.01); *G01N 2800/085* (2013.01)

(58) Field of Classification Search
None
See application file for complete search history.

(56) References Cited

U.S. PATENT DOCUMENTS

| | | | |
|---|---|---|---|
| 5,187,065 A * | 2/1993 | Schutzer | 435/7.32 |
| 8,093,017 B2 * | 1/2012 | Pugia | 435/69.6 |
| 2008/0221305 A1 | 9/2008 | Chen et al. | |
| 2010/0143958 A1 | 6/2010 | Pugia | |

FOREIGN PATENT DOCUMENTS

| | | |
|---|---|---|
| EP | 1870710 A1 | 12/2007 |
| WO | WO 2005/001061 A2 | 1/2005 |
| WO | WO 2010/123720 A1 | 10/2010 |

OTHER PUBLICATIONS

Sahu et al., Structure and biology of complement protein C3, a connecting link between innate and acquired immunity, Immunological Reviews, vol. 180, 2001, pp. 35-48.*
PCT International Search Report and Written Opinion dated Aug. 3, 2012 (15 Pages).
European Search Report dated Mar. 18, 2015 (8 pages).

* cited by examiner

*Primary Examiner* — Gary W Counts
(74) *Attorney, Agent, or Firm* — Kevin Stein

(57) ABSTRACT

Methods of detecting a first species' Ig-CTF in a biological sample comprising exposing the biological sample to a first antibody of a second species that preferentially binds the first species' Ig-CTF or an antigen binding fragment of the antibody, forming a mixture, exposing the mixture to a second antibody or antigen-binding fragment of a third species that preferentially binds the first species' Ig, and detecting the Ig-CTF in the biological sample.

7 Claims, 4 Drawing Sheets

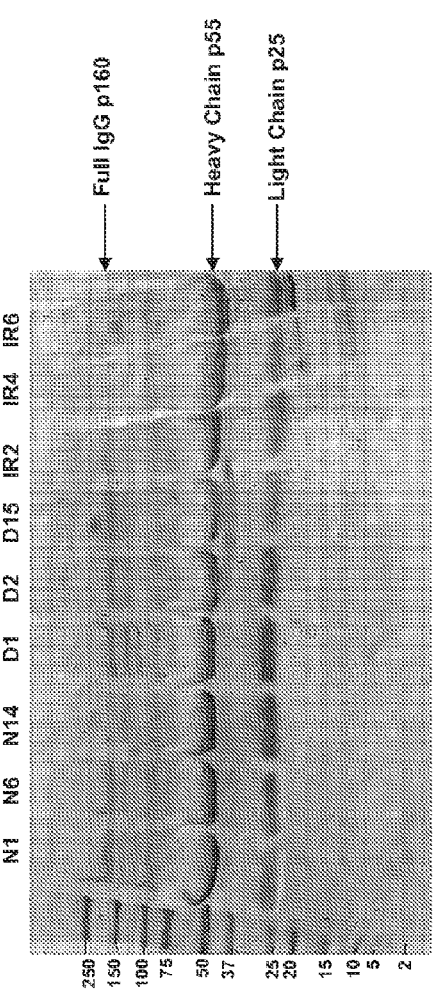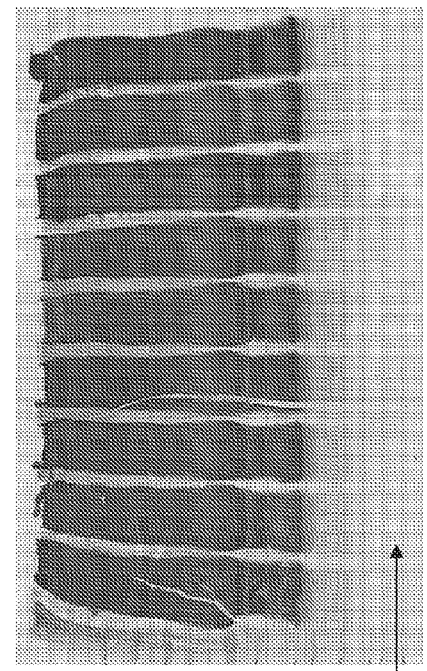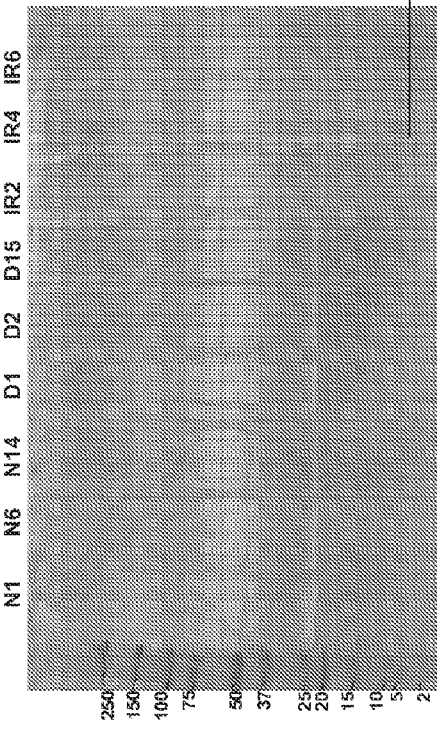

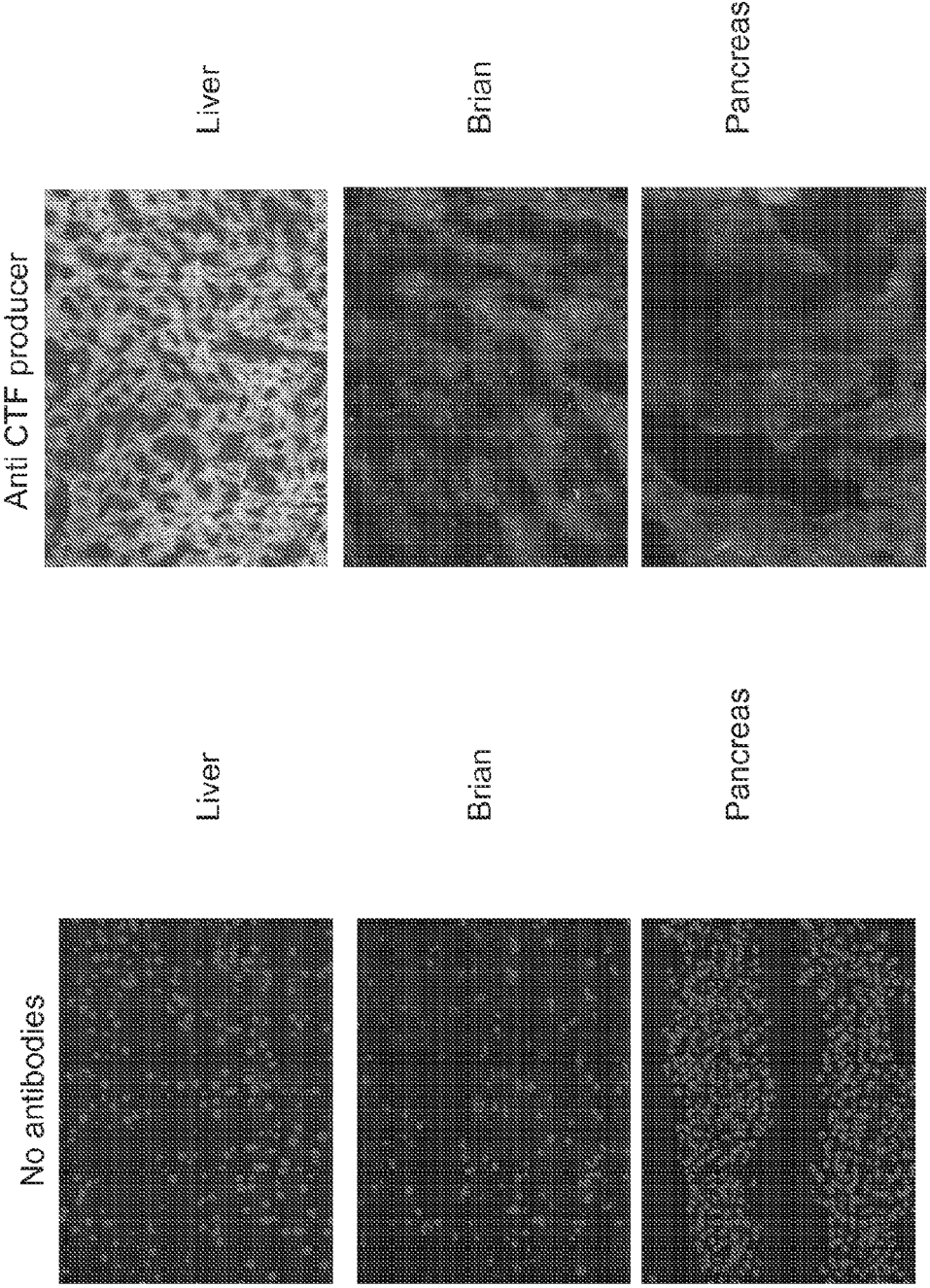

```
                        SEQUENCE LISTING

<160> NUMBER OF SEQ ID NOS: 52

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Val Leu Val Val Ala Ala Ala Phe Val His Phe Tyr Gly Val Ser Asn
1               5                   10                  15

Leu Gln Glu Phe Arg Tyr Gly Leu Glu Gly Gly Cys Thr Asp Asp Thr
            20                  25                  30

Leu Leu

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Val Val Ala Ala Ala Phe Val His Phe Tyr Gly Val Ser Asn Leu
1               5                   10                  15

Gln Glu Phe Arg Tyr Gly Leu Glu Gly Gly Cys Thr Asp Asp Thr Leu
            20                  25                  30

Leu

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Asn Leu Gln Glu Phe Arg Tyr Gly Leu Glu Gly Gly Cys Thr Asp
1               5                   10                  15

Asp Thr Leu Leu
            20

<210> SEQ ID NO 4
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 4

Val Val Ala Ala Ala Phe Val His Phe Tyr Gly Val Ser Asn Leu Gln
1               5                   10                  15

Glu Phe Arg Tyr Gly Leu Glu Gly Gly Cys Thr Asp Asp Thr Leu Leu
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Val Ala Ala Ala Phe Val His Phe Tyr Gly Val Ser Asn Leu Gln Glu
1               5                   10                  15

Phe Arg Tyr Gly Leu Glu Gly Gly Cys Thr Asp Asp Thr Leu Leu
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Ala Ala Phe Val His Phe Tyr Gly Val Ser Asn Leu Gln Glu Phe
1               5                   10                  15

Arg Tyr Gly Leu Glu Gly Gly Cys Thr Asp Asp Thr Leu Leu
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Phe Val His Phe Tyr Gly Val Ser Asn Leu Gln Glu Phe Arg
1               5                   10                  15

Tyr Gly Leu Glu Gly Gly Cys Thr Asp Asp Thr Leu Leu
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Phe Val His Phe Tyr Gly Val Ser Asn Leu Gln Glu Phe Arg Tyr
1               5                   10                  15

Gly Leu Glu Gly Gly Cys Thr Asp Asp Thr Leu Leu
            20                  25
```

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Phe Val His Phe Tyr Gly Val Ser Asn Leu Gln Glu Phe Arg Tyr Gly
1               5                   10                  15

Leu Glu Gly Gly Cys Thr Asp Asp Thr Leu Leu
            20                  25
```

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Val His Phe Tyr Gly Val Ser Asn Leu Gln Glu Phe Arg Tyr Gly Leu
1               5                   10                  15

Glu Gly Gly Cys Thr Asp Asp Thr Leu Leu
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

```
His Phe Tyr Gly Val Ser Asn Leu Gln Glu Phe Arg Tyr Gly Leu Glu
1               5                   10                  15

Gly Gly Cys Thr Asp Asp Thr Leu Leu
            20                  25
```

<210> SEQ ID NO 12
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

```
Phe Tyr Gly Val Ser Asn Leu Gln Glu Phe Arg Tyr Gly Leu Glu Gly
1               5                   10                  15

Gly Cys Thr Asp Asp Thr Leu Leu
            20
```

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

```
Tyr Gly Val Ser Asn Leu Gln Glu Phe Arg Tyr Gly Leu Glu Gly Gly
1               5                   10                  15

Cys Thr Asp Asp Thr Leu Leu
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Val Ser Asn Leu Gln Glu Phe Arg Tyr Gly Leu Glu Gly Gly Cys
1               5                   10                  15

Thr Asp Asp Thr Leu Leu
            20

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Ser Asn Leu Gln Glu Phe Arg Tyr Gly Leu Glu Gly Gly Cys Thr
1               5                   10                  15

Asp Asp Thr Leu Leu
            20

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Leu Gln Glu Phe Arg Tyr Gly Leu Glu Gly Gly Cys Thr Asp Asp
1               5                   10                  15

Thr Leu Leu

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Glu Phe Arg Tyr Gly Leu Glu Gly Gly Cys Thr Asp Asp Thr
1               5                   10                  15

Leu Leu

<210> SEQ ID NO 18
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 18

Gln Glu Phe Arg Tyr Gly Leu Glu Gly Gly Cys Thr Asp Asp Thr Leu
1               5                   10                  15

Leu

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Phe Arg Tyr Gly Leu Glu Gly Gly Cys Thr Asp Asp Thr Leu Leu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Phe Arg Tyr Gly Leu Glu Gly Gly Cys Thr Asp Asp Thr Leu Leu
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Tyr Gly Leu Glu Gly Gly Cys Thr Asp Asp Thr Leu Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Gly Leu Glu Gly Gly Cys Thr Asp Asp Thr Leu Leu
1               5                   10

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ile Phe Val Val Ala Gly Ala Phe Val His Phe His Gly Val Ser Asn
1               5                   10                  15

Leu Gln Glu Phe Arg Phe Met Ile Gly Gly Gly Cys Ser Glu Glu Asp
            20                  25                  30

Ala Leu

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Val Ala Gly Ala Phe Val His Phe His Gly Val Ser Asn Leu Gln Glu
1               5                   10                  15

Phe Arg Phe Met Ile Gly Gly Gly Cys Ser Glu Glu Asp Ala Leu
            20                  25                  30

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Asn Leu Gln Glu Phe Arg Phe Met Ile Gly Gly Gly Cys Ser Glu
1               5                   10                  15

Glu Asp Ala Leu
            20

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Phe Val Val Ala Gly Ala Phe Val His Phe His Gly Val Ser Asn Leu
1               5                   10                  15

Gln Glu Phe Arg Phe Met Ile Gly Gly Gly Cys Ser Glu Glu Asp Ala
            20                  25                  30

Leu

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Val Val Ala Gly Ala Phe Val His Phe His Gly Val Ser Asn Leu Gln
1               5                   10                  15

Glu Phe Arg Phe Met Ile Gly Gly Gly Cys Ser Glu Glu Asp Ala Leu
            20                  25                  30

<210> SEQ ID NO 28
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Gly Ala Phe Val His Phe His Gly Val Ser Asn Leu Gln Glu Phe
1               5                   10                  15

Arg Phe Met Ile Gly Gly Gly Cys Ser Glu Glu Asp Ala Leu
            20                  25                  30

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Phe Val His Phe His Gly Val Ser Asn Leu Gln Glu Phe Arg
1               5                   10                  15

Phe Met Ile Gly Gly Gly Cys Ser Glu Glu Asp Ala Leu
            20                  25

<210> SEQ ID NO 30
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Phe Val His Phe His Gly Val Ser Asn Leu Gln Glu Phe Arg Phe
1               5                   10                  15

Met Ile Gly Gly Gly Cys Ser Glu Glu Asp Ala Leu
            20                  25

<210> SEQ ID NO 31
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Val His Phe His Gly Val Ser Asn Leu Gln Glu Phe Arg Phe Met
1               5                   10                  15

Ile Gly Gly Gly Cys Ser Glu Glu Asp Ala Leu
            20                  25

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val His Phe His Gly Val Ser Asn Leu Gln Glu Phe Arg Phe Met Ile
1               5                   10                  15
```

Gly Gly Gly Cys Ser Glu Glu Asp Ala Leu
            20                  25

<210> SEQ ID NO 33
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Phe His Gly Val Ser Asn Leu Gln Glu Phe Arg Phe Met Ile Gly
1               5                   10                  15

Gly Gly Cys Ser Glu Glu Asp Ala Leu
            20                  25

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe His Gly Val Ser Asn Leu Gln Glu Phe Arg Phe Met Ile Gly Gly
1               5                   10                  15

Gly Cys Ser Glu Glu Asp Ala Leu
            20

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Gly Val Ser Asn Leu Gln Glu Phe Arg Phe Met Ile Gly Gly Gly
1               5                   10                  15

Cys Ser Glu Glu Asp Ala Leu
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Val Ser Asn Leu Gln Glu Phe Arg Phe Met Ile Gly Gly Gly Cys
1               5                   10                  15

Ser Glu Glu Asp Ala Leu
            20

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Ser Asn Leu Gln Glu Phe Arg Phe Met Ile Gly Gly Gly Cys Ser
1               5                   10                  15

Glu Glu Asp Ala Leu
            20

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asn Leu Gln Glu Phe Arg Phe Met Ile Gly Gly Gly Cys Ser Glu Glu
1               5                   10                  15

Asp Ala Leu

<210> SEQ ID NO 39
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Gln Glu Phe Arg Phe Met Ile Gly Gly Gly Cys Ser Glu Glu Asp
1               5                   10                  15

Ala Leu

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Glu Phe Arg Phe Met Ile Gly Gly Gly Cys Ser Glu Glu Asp Ala
1               5                   10                  15

Leu

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Phe Arg Phe Met Ile Gly Gly Gly Cys Ser Glu Glu Asp Ala Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 42

Phe Arg Phe Met Ile Gly Gly Gly Cys Ser Glu Glu Asp Ala Leu
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Phe Met Ile Gly Gly Gly Cys Ser Glu Glu Asp Ala Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Met Ile Gly Gly Gly Cys Ser Glu Glu Asp Ala Leu
1               5                   10

<210> SEQ ID NO 45
<211> LENGTH: 467
<212> TYPE: PRT
<213> ORGANISM: Homo sapiens

<400> SEQUENCE: 45

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Val Ala Ser Gly Phe Thr Phe
            35                  40                  45

Ser Ser Tyr Pro Met Thr Trp Val Arg Gln Ala Pro Gly Lys Gly Leu
    50                  55                  60

Glu Trp Val Ala Ser Ile Ser Tyr Asp Gly Ser Tyr Lys Tyr Lys Val
65                  70                  75                  80

Asp Ser Met Lys Gly Arg Leu Thr Ile Ser Arg Asp Asn Ser Lys Asn
                85                  90                  95

Thr Leu Tyr Leu Glu Met Asn Ser Leu Thr Ala Glu Asp Thr Ala Val
            100                 105                 110

Tyr Tyr Cys Ala Arg Thr Ala Phe Phe Asn Ala Tyr Asp Phe Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
```

```
               195                 200                 205
Pro Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Val Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
    450                 455                 460

Pro Gly Lys
465

<210> SEQ ID NO 46
<211> LENGTH: 134
<212> TYPE: PRT
<213> ORGANISM: Homo sapiens

<400> SEQUENCE: 46

Met Arg Leu Pro Ala Gln Leu Leu Gly Leu Leu Met Leu Trp Val Pro
1               5                   10                  15

Gly Ser Ser Gly Asp Val Val Met Thr Gln Ser Pro Leu Ser Leu Pro
                20                  25                  30

Val Thr Leu Gly Gln Pro Ala Ser Ile Ser Cys Arg Ser Ser Gln Ser
            35                  40                  45

Leu Val His Ser Asp Gly Asn Thr Tyr Leu Asn Trp Phe Gln Gln Arg
        50                  55                  60

Pro Gly Gln Ser Pro Arg Arg Leu Ile Tyr Arg Val Ser Asn Arg Asp
65                  70                  75                  80

Ser Gly Val Pro Asp Arg Phe Ser Gly Ser Gly Ser Gly Thr Asp Phe
                85                  90                  95
```

```
Thr Leu Lys Ile Ser Arg Val Glu Ala Glu Asp Val Gly Leu Tyr Tyr
            100                 105                 110

Cys Met Gln His Thr His Trp Ser Pro Ile Thr Phe Gly Gln Gly Thr
        115                 120                 125

Arg Leu Glu Ile Lys Arg
    130

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Gly Gly Cys Thr Asp Asp Thr Leu Leu
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Gly Cys Ser Glu Glu Asp Ala Leu
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Val Leu Val Val Ala Ala Ala Phe Val His Phe Cys Tyr Ser
1               5                   10                  15

<210> SEQ ID NO 50
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Phe Tyr Gly Val Ser Asn Leu Gln Glu Phe Arg Tyr Gly Leu Glu
1               5                   10                  15

Gly Gly Cys Thr Asp Asp Ser Leu Leu
            20                  25

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

```
Gly Gly Cys Thr Asp Asp Thr Leu Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Cys Ser Glu Glu Asp Ala Leu
1               5
```

ADIPONECTIN RECEPTOR C-TERMINAL FRAGMENTS (CTF)-IMMUNOGLOBULIN

CROSS REFERENCE TO RELATED APPLICATIONS

This application claims the benefit of U.S. Provisional Application No. 61/445,103 filed Feb. 22, 2011, which is incorporated herein by reference in its entirety. The following applications and publications also are incorporated herein by reference in their entireties:
U.S. application Ser. No. 10/572,882 (U.S. Publ. No. 2007/0053913), which is the national stage of International Appl. No. PCT/EP2004/10383;
U.S. application Ser. No. 10/572,883 (U.S. Publ. No. 2007/0037226), which is the national stage of International Appl. No. PCT/EP2004/10384;
U.S. Application No. 60/748,305;
International Publ. No. WO2007/120311;
U.S. Application No. 60/991,328;
U.S. Publication No. 2011/0301089;
U.S. application Ser. No. 12/169,983 (U.S. Pat. No. 8,017,573); and
U.S. application Ser. No. 13/265,968 (Intl. Publ. No. WO 2010/123720).

This application incorporates by reference the sequence listing which is submitted together with this application in computer readable form which has the file name Sequence_Listing_CRF_SMSD0095.TXT and is 22.0 KB.

TECHNICAL FIELD

The subject matter provided herein relates generally to methods, kits, and agents for the detection of Ig-CTF as well as for the diagnosis, treatment, and monitoring of diabetes, cancer, and liver disease.

BACKGROUND

Obesity with chronic inflammation affects a large and growing population. This population has a high risk for developing cardiovascular disease and diabetes and frequently develops metabolic syndromes associated with insulin resistance. Recently, adiponectin and other adipokines have been discovered as fat cell hormones that control glucose metabolism. Both type and location of fat cells are important. Obesity produces additional adipocytes which secrete adiponectin into the blood, helping muscle cell metabolism of fats and glucose. Some overweight patients become insulin resistant. In this case, adipocytes stop producing adiponectin. Levels of adiponectin in the blood are decreased under conditions of obesity, insulin resistance and Type 2 diabetes. Methods exist for measuring adiponectin levels in subjects for the prognosis of these and other disease states. Measurement of adiponectin levels, however, has proven to be a weak indicator of disease. A need exists for better methods of monitoring disease states associated with abnormal adipocyte activity. The present invention provides this and other needs.

Adiponectin Receptor 1 (ADIPOR1) is a seven transmembrane G protein coupled receptor (GPCR). See, for example, WO 01/012662 and WO 01/090304. Many medically significant biological processes are mediated by signal transduction pathways that involve G-proteins [Lefkowitz, Nature 351, 353-354 (1991)]. Certain extracellular messengers (ECM), which are peptide fragments from the C-terminal of ADIPOR1, have diagnostic value in human blood. Their usefulness was confirmed using a polyclonal antibody with a mass measuring SELDI-TOF immuno-affinity method. Those inventions are the subject of related application WO 2007/120,311, which is incorporated herein by reference.

SUMMARY

It was unexpectedly discovered that C-terminal fragments (CTF) of ADIPOR1 and ADIPOR2 (SEQ ID NOs: 1 to 44) are covalently integrated into immunoglobulin gamma and kappa chains as part of the protein structure. Additionally it was found that CTF-immunoglobulin was in the plasma, cells and tissues of patients and that changes in CTF-immunoglobulin correlated with insulin resistance and cancer in patients. Accordingly, the CTF portion of CTF-immunoglobulin was found to reduce cellular insulin response thus causing the expected inhibition of cell growth and reduced ability to lower blood glucose level.

The immunoglobulin portion of CTF-immunoglobulin was found to bind to antigens in cells, tissues, and blood. Binding of antigens leads to Ig-CTF leaving the plasma and entering cells and tissues, inhibiting cell growth and reducing insulin response. Accordingly, the immunoglobulin portion of CTF-immunoglobulin and antigens thereof are useful in methods for directing whether CTF enters cells and tissue. Further, the immunoglobulin portion of CTF-immunoglobulin and the antigens bound can be measured and used to improve diagnostic measurements of CTF.

Provided herein are methods of treating insulin resistance and/or inhibiting cell growth in a patient in need thereof, comprising the step of: administering to said patient an effective amount of a CTF peptide or a pharmaceutically acceptable salt thereof covalently integrated to immunoglobulin as part of the protein structure; wherein the peptide has at least 75% identity with SEQ ID NOs: 1 to 44 wherein the peptide is covalently attached to gamma and kappa and immunoglobulin chains of at least 75% identity with SEQ ID NOs: 45 and 46.

Also provided are methods of treating insulin resistance and inhibition of cell growth in a patient in need thereof, comprising the step of: administering to said patient an effective amount of the immunoglobulin that binds to CTF, wherein immunoglobulin binds a peptide that has at least 75% identity with SEQ ID NOs: 1 to 44.

Also provided are methods of treating insulin resistance and methods of inhibiting cell growth in a patient in need thereof, comprising the step of: administering to said patient an effective amount of the immunoglobulin that has at least 75% identity with the gamma or kappa chains in CTF immunoglobulin.

Further disclosed herein are methods of treating insulin resistance and methods of inhibiting cell growth in a patient in need thereof, comprising the step of: administering to said patient an effective amount of a peptide antigen or a pharmaceutically-acceptable salt thereof shown to bind to the immunoglobulin portions of CTF immunoglobulin.

Methods of diagnosing insulin resistance and/or abnormal cell growth in a patient in need thereof by measuring the CTF peptide and immunoglobulin portion in a biological sample of the patient, wherein said CTF peptide has at least 75% identity with an amino acid sequence of SEQ ID NOs: 1 to 44 and wherein the immunoglobulin portion has at least 75% identity with a gamma or kappa immunoglobulin chain comprising the amino acid sequence of SEQ ID NO: 45 or SEQ ID NO: 46, are further provided.

Further described are methods of diagnosing insulin resistance and/or abnormal cell growth in a patient in need thereof, by measuring the immunoglobulin portion of CTF immunoglobulin in a biological sample of the patient, wherein the immunoglobulin portion has at least 75% identity with a gamma or kappa immunoglobulin chain comprising the amino acid sequence of SEQ ID NO: 45 or SEQ ID NO: 46.

Also provided are methods of diagnosing insulin resistance and/or abnormal cell growth in a patient in need thereof, by measuring the peptide antigen shown to bind to the immunoglobulin portion of CTF immunoglobulin in a biological sample of the patient, wherein the immunoglobulin portion has at least 75% identity with a gamma heavy chain or a kappa light chain comprising the amino acid sequence of SEQ ID NO: 45 or SEQ ID NO: 46.

In some embodiments are provided methods of detecting a first species' Ig-CTF in a biological sample comprising exposing the biological sample to a first antibody of a second species that preferentially binds the first species' Ig-CTF or an antigen binding fragment of the antibody, thereby forming a mixture, exposing the mixture to a second antibody or antigen-binding fragment of a third species that preferentially binds the first species' Ig, and detecting the Ig-CTF in said biological sample.

Also provided are methods for diagnosing insulin resistance in a subject of a first species, the method comprising exposing a biological sample derived from the subject to a first antibody of a second species that preferentially binds the first species' Ig-CTF or an antigen-binding fragment of the antibody, thereby forming a mixture, exposing the mixture to a second antibody or antigen-binding fragment of a third species that preferentially binds the first species' Ig, quantifying the amount of Ig-CTF present in said sample, comparing the amount of Ig-CTF present in the sample to a known standard, and determining whether the amount of Ig-CTF in the sample falls within the level of Ig-CTF associated with insulin resistance.

Also provided are methods for diagnosing cancer in a subject of a first species, said method comprising exposing a biological sample derived from the subject to a first antibody of a second species that preferentially binds the first species' Ig-CTF or an antigen-binding fragment thereof to form a mixture, exposing the mixture to a second antibody or antigen-binding fragment of a third species that preferentially binds the first species' Ig, quantifying the amount of Ig-CTF present in said sample, comparing the amount of Ig-CTF present in the sample to a known standard, and determining whether the amount of Ig-CTF in the sample falls within the level of Ig-CTF associated with cancer.

Methods for treating insulin resistance in a subject of a first species are provided, the method comprising exposing a biological sample derived from the subject to a first antibody of a second species that preferentially binds the first species' Ig-CTF or an antigen-binding fragment thereof, thereby forming a mixture, exposing the mixture to a second antibody or antigen-binding fragment of a third species that preferentially binds the first species' Ig, quantifying the amount of Ig-CTF present in the sample, comparing the amount of Ig-CTF present in the sample to a known standard, determining whether the amount of Ig-CTF in the sample falls within the level of Ig-CTF associated with insulin resistance, and administering to the subject, or prescribing, a treatment for insulin resistance.

Also provided are methods of treating cancer in a subject of a first species, said method comprising exposing a biological sample derived from the subject to a first antibody of a second species that preferentially binds the first species' Ig-CTF or an antigen-binding fragment thereof, thereby forming a mixture, exposing said mixture to a second antibody or antigen-binding fragment of a third species that preferentially binds the first species' Ig, quantifying the amount of Ig-CTF present in said sample, comparing the amount of Ig-CTF present in the sample to a known standard, determining whether the amount of Ig-CTF in the sample falls within the level of Ig-CTF associated with cancer, and administering to the subject, or prescribing, a treatment for cancer.

Further provided herein are kits for detecting the presence of Ig-CTF in a biological sample, the kit comprising a first isolated antibody that preferentially binds Ig CTF produced by the cell line deposited with the ATCC having accession number 444-1D12.1H7 (mAb 444-1D12), a first isolated antibody that preferentially binds CTF produced by the cell line deposited with the ATCC having accession number 510-6B6.1G1 (mAb-510-6B6), and/or a first isolated antibody that preferentially binds CTF produced by the cell line deposited with the ATCC having accession number 515-4D6.1B10 (mAb-515-4D6), a second antibody or antigen-binding fragment that preferentially binds human Ig, and instructions for use of the first antibody or antigen-binding fragment and the second antibody or antigen-binding fragment together with packaging for the same.

Also disclosed are methods of monitoring insulin resistance in a subject of a first species, said methods comprising exposing a biological sample obtained from said subject to a first antibody of a second species that preferentially binds the first species' Ig-CTF or an antigen-binding fragment thereof, thereby forming a mixture, exposing said mixture to a second antibody or antigen-binding fragment of a third species that preferentially binds the first species' Ig, quantifying the amount of Ig-CTF present in said sample, comparing the amount of Ig-CTF present in the sample to either i. a known standard or ii. the amount of Ig-CTF present in a biological sample obtained from the subject at an earlier point in time, and determining whether the subject's level of Ig-CTF is indicative of progression, regression, or stabilization of insulin resistance.

In some embodiments are provided methods of monitoring cancer in a subject of a first species, said methods comprising exposing a biological sample obtained from said subject to a first antibody of a second species that preferentially binds the first species Ig-CTF or an antigen-binding fragment thereof, thereby forming a mixture, exposing said mixture to a second antibody or antigen-binding fragment of a third species that preferentially binds the first species' Ig, quantifying the amount of Ig-CTF present in said sample, comparing the amount of Ig-CTF present in the sample to either i. a known standard or ii. the amount of Ig-CTF present in a biological sample obtained from the subject at an earlier point in time, and determining whether the subject's level of Ig-CTF is indicative of progression, regression, or stabilization of cancer.

Further provided herein are methods of monitoring the level of Ig-CTF in a subject of a first species, said method comprising exposing a biological sample obtained from the subject to a first antibody of a second species that preferentially binds the first species' Ig-CTF or an antigen-binding fragment thereof, forming a mixture, exposing said mixture to a second antibody or antigen-binding fragment of a third species that preferentially binds the first species' Ig, quantifying the amount of Ig-CTF present in the sample, comparing the amount of Ig-CTF present in the sample to either i. a known standard or ii. the amount of Ig-CTF present in a biological sample obtained from the subject at an earlier point in time.

Methods for diagnosing liver disease in a subject of a first species also are disclosed, said methods comprising exposing a biological sample derived from the subject to a first antibody of a second species that preferentially binds the first species' Ig-CTF or an antigen-binding fragment thereof, thereby forming a mixture, exposing the mixture to a second antibody or an antigen-binding fragment of a third species that preferentially binds the first species' Ig, quantifying the amount of Ig-CTF present in the sample, comparing the amount of Ig-CTF present in the sample to a known standard, and determining whether the amount of Ig-CTF in the sample falls within the level of Ig-CTF associated with liver disease.

In some embodiments are provided methods of treating liver disease in a subject of a first species, said methods comprising exposing a biological sample derived from the subject to a first antibody of a second species that preferentially binds the first species' Ig-CTF or an antigen-binding fragment thereof, thereby forming a mixture, exposing the mixture to a second antibody or antigen-binding fragment of a third species that preferentially binds the first species' Ig, quantifying the amount of Ig-CTF present in the sample, comparing the amount of Ig-CTF present in the sample to a known standard, determining whether the amount of Ig-CTF in the sample falls within the level of Ig-CTF associated with liver disease, and administering to the subject, or prescribing, a treatment for liver disease.

Also provided are methods of monitoring liver disease in a subject of a first species, said methods comprising exposing a biological sample obtained from the subject to a first antibody of a second species that preferentially binds the first species Ig-CTF or an antigen-binding fragment thereof, forming a mixture, exposing said mixture to a second antibody or antigen-binding fragment of a third species that preferentially binds the first species' Ig, quantifying the amount of Ig-CTF present in said sample, comparing the amount of Ig-CTF present in the sample to either i. a known standard, or ii. the amount of Ig-CTF present in a biological sample obtained from the subject at an earlier point in time, and determining whether the subject's level of Ig-CTF is indicative of progression, regression, or stabilization of liver disease in the subject.

In another aspect are provided isolated polypeptides comprising the amino acid sequence of SEQ ID NO: 49 (Antigen used to make the cell line that makes the antibody mAb 461-4H11 deposited with the ATCC on Feb. 21, 2012 having accession number 461-4H11.2A4), SEQ ID NO: 50 (Antigen used to make the cell line that makes the antibody mAb 444-1D12 deposited with the ATCC on Feb. 21, 2012 having accession number 444-1D12.1H7), SEQ ID NO: 51 (Antigen used to make the cell line that makes the antibody mAb 515-4D6 deposited with the ATCC on Feb. 21, 2012 having accession number 515-4D6.1B10), and SEQ ID NO: 52 (Antigen used to make the cell line that makes the antibody mAb 510-6B6 deposited with the ATCC on Feb. 21, 2012 having accession number 510-6B6.1G1). Also provided are isolated polypeptide complexes comprising any one of the amino acid sequences of SEQ ID NOs: 1 to 44 covalently attached to the amino acid sequence of SEQ ID NO: 45 or SEQ ID NO: 46 or to fragments thereof.

Further provided are methods for detecting Ig-CTF in a biological sample, said method comprising exposing a biological sample derived from a subject of a first species to a first antibody of a second species that preferentially binds the first species' Ig-CTF or an antigen-binding fragment thereof, forming a mixture, exposing the mixture to a second antibody or an antigen-binding fragment of a third species that preferentially binds the first species' Ig, and detecting the Ig-CTF present in the sample.

In some embodiments, the first species, the second species, and the third species are not the same species. In some embodiments, the Ig-CTF comprises a C-terminal fragment of AdipoR1 covalently attached to an Ig. In some embodiments, the C-terminal fragment of AdipoR1 comprises any one of the amino acid sequences of SEQ ID NOs: 1 to 22. In some embodiments, the Ig-CTF comprises a C-terminal fragment of AdipoR2 covalently attached to an Ig. In other suitable embodiments, the C-terminal fragment of AdipoR2 comprises any one of the amino acid sequences of SEQ ID NOs: 23-44. In some embodiments, the Ig-CTF comprises a C-terminal fragment of AdipoR1 covalently attached to an Ig and a C-terminal fragment of AdipoR2 covalently attached to an Ig. In some embodiments, the step of exposing a biological sample derived from the subject to a first antibody of a second species that preferentially binds the first species' Ig-CTF or an antigen-binding fragment thereof encompasses exposing the biological sample to more than one such first antibody of a second species that preferentially binds the first species' Ig-CTF or antigen-binding fragment.

In some embodiments, the biological sample is derived or obtained from urine, blood, serum, plasma, saliva, ascites, circulating cells, circulating tumor cells, cells that are not tissue associated, tissues, surgically resected tumor tissue, biopsies, fine needle aspiration samples, cerebrospinal fluid, interstitial fluid, white blood cells, interstitial fluids or histological preparations. In preferred embodiments, the biological sample is derived from blood or plasma. Fluoride, heparin, or EDTA can be added to the biological sample. The tissue can be liver, pancreas, lymph node, adipose, muscle, or brain.

The biological sample can be derived from a mammal and that mammal can be a human, a non-human primate. Alternatively, the mammal can be a mouse, rat, guinea pig, hamster, dog, cat, sheep, cow, horse, donkey, mule, or pig.

In some embodiments, the first antibody or antigen-binding fragment is bound to a solid support and that solid support can be an enzyme immunoassay (EIA) or radioimmunoassay (RIA) plate.

In some embodiments, the second antibody or antigen-binding fragment is detectably labeled. For example, the detectable label can be a radiolabel, chemiluminescence label, a fluorescent label, an epitope tag, biotin, a chromophore label, an electrochemiluminescence (ECL) label, or an enzyme (e.g., alkaline phosphatase).

In suitable embodiments, the first antibody comprises: an isolated antibody that preferentially binds IgCTF produced by the cell line deposited with the ATCC having accession number 444-1D12.1H7 (mAb 444-1D12), an isolated antibody that preferentially binds CTF produced by the cell line deposited with the ATCC having accession number 510-6B6.1G1 (mAb-510-6B6), or an isolated antibody that preferentially binds CTF produced by the cell line deposited with the ATCC having accession number 515-4D6.1B10 (mAb-515-4D6). In some embodiments, the first antibody comprises two or more of these antibodies.

In some embodiments, the immunoglobulin ("Ig") is IgG, IgA, IgM, IgD, or IgE. In preferred embodiments, the Ig is IgG. In other embodiments, the Ig is a Kappa light chain of IgG, IgM, or IgA or the Ig is a Gamma heavy chain of IgG. In another embodiment, the Ig is an antigen binding region (Fab). In some embodiments, the step of exposing the mixture to a second antibody or antigen-binding fragment of a third species that preferentially binds the first species' Ig encompasses exposing the mixture to more than one such second antibody or antigen-binding fragment of a third species that preferentially binds the first species' Ig. In other embodiments, the more than one such second antibody or antigen-binding fragment of a third species that preferentially binds the first species' Ig can bind IgG, IgA, IgM, IgD, IgE, a Kappa light chain of IgG, IgM, or IgA, a Gamma heavy chain of IgG, an antigen binding region (Fab) or any combination thereof.

In some preferred embodiments, free CTF is not being detected.

In some embodiments, the insulin resistance is associated with impaired glucose tolerance, prediabetes, type 1 diabetes, type 2 diabetes, type 3 diabetes, juvenile diabetes, gestational diabetes, or nonalcoholic steatohepatitis (NASH).

In some embodiments, the cancer is breast cancer, metastatic cancer, pancreatic cancer, or hepatocellular carcinoma.

In some embodiments, the liver disease is autoimmune hepatitis, nonalcoholic steatohepatitis (NASH), or alcoholic hepatitis.

BRIEF DESCRIPTION OF THE DRAWINGS

The accompanying drawings are nonlimiting and are included to provide a further understanding of the embodiments described herein and are incorporated in and constitute a part of this specification.

FIG. 3 shows CTF is bonded to immunoglobulins. FIG. 3a shows the denatured western blot result for plasma from 3 normal human patients, 3 diabetic patients and 3 impaired glucose tolerance patients. The CTF antibody detects bands of various molecular weights representing covalently bound immunoglobulin. The western blots for the same samples treated with base conditions are shown in FIG. 3b. CTF bands are no longer evident presumably because the bond has been broken. These same samples were tested in FIG. 3c with and anti-IgG antibody to show that the immunoglobulin remains.

FIG. 4 shows example images of increased absorption of IgG-CTF and CTF into the liver, brain and pancreas in rabbits producing antibodies to CTF.

DETAILED DESCRIPTION OF ILLUSTRATIVE EMBODIMENTS

Figure 1:
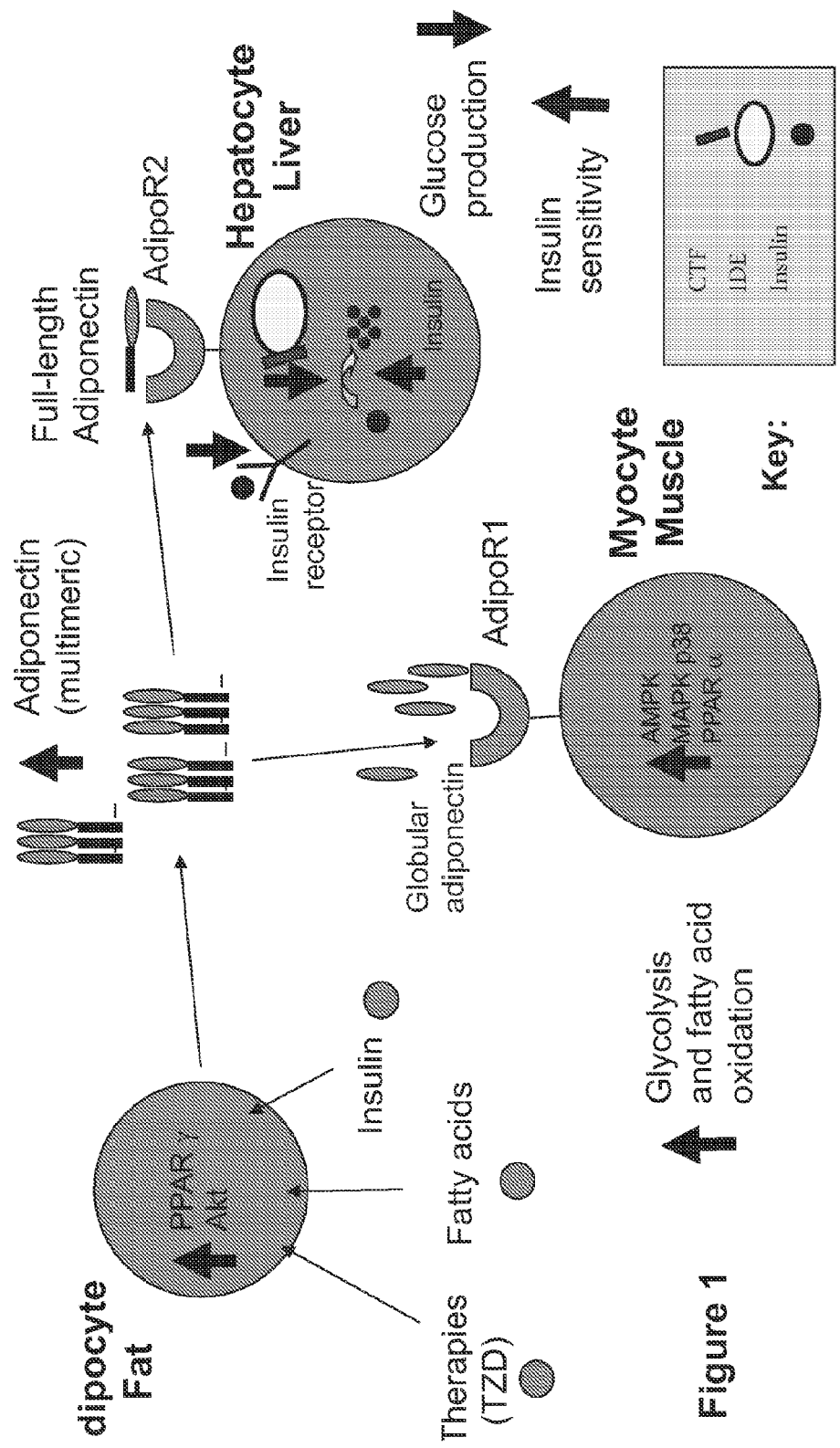
FIG. 1 illustrates a proposed mechanism of adiponectin on adiponectin receptor response. In normal patients, adiponectin activates the adiponectin receptor signaling pathways of AMPK MAPK p38 and PPAR α causing glycolysis and fatty acid oxidation in muscles and slowing glucose production in the liver. Adiponectin does not directly bind the C-terminal fragments of adiponectin or activate release of CTF. Instead, adiponectin blocks C-terminal fragment release. This sensitizes cells to insulin as CTF is not released to inhibit insulin degradation enzyme (IDE) in the liver. This allows IDE to degrade intercellular insulin which maintains stronger insulin receptor response.

Each of the patents, patent application, publications, and references cited herein is incorporated by reference in its entirety.

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations of ±20%, preferably ±10%, more preferably ±5%, even more preferably ±1%, and yet even more preferably ±0.1% from the specified value, as such variations are appropriate to perform the disclosed methods and compositions.

As used herein, CTF includes amino acid sequences shown in Table 1 and sequences having at least 75%, preferably at least 85%, more preferably at least 90%, and even more preferably at least 95% identity thereto.

TABLE 1

| SEQ ID NO: | Designation | Amino Acid Sequence |
|---|---|---|
| 1 | Fragment 1 of AdipoR1 | VLVVAAAFVHFYGVSNLQEFRYGLEGGCTDDTLL |
| 2 | Fragment 2 of AdipoR1 | LVVAAAFVHFYGVSNLQEFRYGLEGGCTDDTLL |
| 3 | Fragment 3 of AdipoR1 | SNLQEFRYGLEGGCTDDTLL |
| 4 | Fragment 4 of AdipoR1 | VVAAAFVHFYGVSNLQEFRYGLEGGCTDDTLL |
| 5 | Fragment 5 of AdipoR1 | VAAAFVHFYGVSNLQEFRYGLEGGCTDDTLL |
| 6 | Fragment 6 of AdipoR1 | AAAFVHFYGVSNLQEFRYGLEGGCTDDTLL |
| 7 | Fragment 7 of AdipoR1 | AAFVHFYGVSNLQEFRYGLEGGCTDDTLL |
| 8 | Fragment 8 of AdipoR1 | AFVHFYGVSNLQEFRYGLEGGCTDDTLL |
| 9 | Fragment 9 of AdipoR1 | FVHFYGVSNLQEFRYGLEGGCTDDTLL |
| 10 | Fragment 10 of AdipoR1 | VHFYGVSNLQEFRYGLEGGCTDDTLL |
| 11 | Fragment 11 of AdipoR1 | HFYGVSNLQEFRYGLEGGCTDDTLL |
| 12 | Fragment 12 of AdipoR1 | FYGVSNLQEFRYGLEGGCTDDTLL |
| 13 | Fragment 13 of AdipoR1 | YGVSNLQEFRYGLEGGCTDDTLL |
| 14 | Fragment 14 of AdipoR1 | GVSNLQEFRYGLEGGCTDDTLL |
| 15 | Fragment 15 of AdipoR1 | VSNLQEFRYGLEGGCTDDTLL |
| 16 | Fragment 16 of AdipoR1 | NLQEFRYGLEGGCTDDTLL |
| 17 | Fragment 17 of AdipoR1 | LQEFRYGLEGGCTDDTLL |
| 18 | Fragment 18 of AdipoR1 | QEFRYGLEGGCTDDTLL |

TABLE 1-continued

| SEQ ID NO: | Designation | Amino Acid Sequence |
|---|---|---|
| 19 | Fragment 19 of AdipoR1 | EFRYGLEGGCTDDTLL |
| 20 | Fragment 20 of AdipoR1 | FRYGLEGGCTDDTLL |
| 21 | Fragment 21 of AdipoR1 | RYGLEGGCTDDTLL |
| 22 | Fragment 22 of AdipoR1 | YGLEGGCTDDTLL |
| 23 | Fragment 1 of AdipoR2 | IFVVAGAFVHFHGVSNLQEFRFMIGGGCSEEDAL |
| 24 | Fragment 2 of AdipoR2 | VAGAFVHFHGVSNLQEFRFMIGGGCSEEDAL |
| 25 | Fragment 3 of AdipoR2 | SNLQEFRFMIGGGCSEEDAL |
| 26 | Fragment 4 of AdipoR2 | FVVAGAFVHFHGVSNLQEFRFMIGGGCSEEDAL |
| 27 | Fragment 5 of AdipoR2 | VVAGAFVHFHGVSNLQEFRFMIGGGCSEEDAL |
| 28 | Fragment 6 of AdipoR2 | AGAFVHFHGVSNLQEFRFMIGGGCSEEDAL |
| 29 | Fragment 7 of AdipoR2 | GAFVHFHGVSNLQEFRFMIGGGCSEEDAL |
| 30 | Fragment 8 of AdipoR2 | AFVHFHGVSNLQEFRFMIGGGCSEEDAL |
| 31 | Fragment 9 of AdipoR2 | FVHFHGVSNLQEFRFMIGGGCSEEDAL |
| 32 | Fragment 10 of AdipoR2 | VHFHGVSNLQEFRFMIGGGCSEEDAL |
| 33 | Fragment 11 of AdipoR2 | HFHGVSNLQEFRFMIGGGCSEEDAL |
| 34 | Fragment 12 of AdipoR2 | FHGVSNLQEFRFMIGGGCSEEDAL |
| 35 | Fragment 13 of AdipoR2 | HGVSNLQEFRFMIGGGCSEEDAL |
| 36 | Fragment 14 of AdipoR2 | GVSNLQEFRFMIGGGCSEEDAL |
| 37 | Fragment 15 of AdipoR2 | VSNLQEFRFMIGGGCSEEDAL |
| 38 | Fragment 16 of AdipoR2 | NLQEFRFMIGGGCSEEDAL |
| 39 | Fragment 17 of AdipoR2 | LQEFRFMIGGGCSEEDAL |
| 40 | Fragment 18 of AdipoR2 | QEFRFMIGGGCSEEDAL |
| 41 | Fragment 19 of AdipoR2 | EFRFMIGGGCSEEDAL |
| 42 | Fragment 20 of AdipoR2 | FRFMIGGGCSEEDAL |
| 43 | Fragment 21 of AdipoR2 | RFMIGGGCSEEDAL |
| 44 | Fragment 22 of AdipoR2 | FMIGGGCSEEDAL |

As used herein, "immunoglobulin gamma heavy chain" or "immunoglobulin light chain" includes the respective amino acid sequence shown in Table 2 and sequences having at least 75%, preferably at least 85%, more preferably at least 90%, more preferably at least 95% identity, and even more preferably at least 98% or 99% identity thereto.

TABLE 2

| SEQ ID NO: | Immunoglobulin Chain | Amino Acid Sequence |
|---|---|---|
| 45 | Gamma Heavy | MEFGLSWVFL VALLRGVQCQ VQLVESGGGV VQPGRSLRLS CVASGFTFSS YPMTWVRQAP GKGLEWVASI SYDGSYKYKV DSMKGRLTIS RDNSKNTLYL EMNSLTAEDT AVYYCARTAF FNAYDFWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS VGSFFLYSKL TVDKSRWQQG NVFSCSVMHE ALHNHYTQKS LSLSPGK |
| 46 | Kappa Light | MRLPAQLLGL LMLWVPGSSG DVVMTQSPLS LPVTLGQPAS ISCRSSQSLV HSDGNTYLNW FQQRPGQSPR RLIYRVSNRD SGVPDRFSGS GSGTDFTLKI SRVEAEDVGL YYCMQHTHWS PITFGQGTRL EIKR |

As used herein, the term "immunoglobulin" or "Ig" refers to an antibody directed at antigen including IgG, IgA, IgM, IgD and IgE class and fragments thereof containing an antigen binding region (Fab), an immunoglobulin kappa light chain, or immunoglobulin gamma heavy chain, such as for example, an immunoglobulin chain comprising SEQ ID NO: 45 or 46. Further the term "immunoglobulin" comprises immunoglobulin from all species expressing adiponectin receptor whether it is a native or modified immunoglobulin such as humanized antibodies, chimeric antibodies, bifunctional antibodies or recombinant antibodies prepared based on a homologous sequence.

As used herein, "attached" means covalent attachment by a chemical bond. When used in reference to Ig-CTF, "attached" refers to a covalent chemical bond between a CTF comprising an amino acid sequence of SEQ ID NOs: 1 to 44 and an immunoglobulin.

For example, when used in reference to Ig-CTF, "attached" includes attachment of CTF forming an ester or amide with a residue in SEQ ID NOs: 45 or 46. While not being bound to the mechanism, the covalent attachment is thought to occur after an activated internal thioester is formed in CTF between cysteine and glutamine in the peptide sequence (SEQ ID NOs: 1 to 44). This activated thioester is able to form a bond with immunoglobulin when immunoglobulin is brought into proximity of the thioester. This proposed mechanism of attachment is thought to be similar to the attachment process of complement C3b to antigens which occurs through an internal thioester as shown in:

Sim R. B. and Twose T M, R. C. The covalent-binding reaction of complement component C3 Biochem J 193; 115-27 (1981);

Lutz H. U. and Stammler P. Preferential formation of C3b-IgG Complexes in vitro and in vivo from nascent C3b and naturally occurring anti-band 3 antibodies J Bio Chem 268, 17418-426, 1993; and Suhn A and Pangburn M K. Covalent Attachment of Human Complement C3 to IgG J Bio Chem 269, 28997-29002, 1994.

Further "attached" via means via a mechanism whereby CTF is activated as an internal thioester between cysteine and glutamic acids in the peptide R1 CTF sequence (SEQ ID NO: 47) Glu-Gly-Gly-Cys-Thr-Asp-Asp-Thr-Leu-Leu. The amino acid sequence of SEQ ID NO: 47 occurs in many of the CTF AdipoR1 sequences, such as in SEQ ID NOs: 1 to 22. In the R2 CTF sequence (SEQ ID NO:48), the amino acid sequence is Gly-Gly-Gly-Cys-Ser-Glu-Glu-Asp-Ala-Leu. The amino acid sequence of SEQ ID NO: 48 occurs in many of the CTF AdipoR2 sequences, such as in SEQ ID NOs: 23 to 44.

Further "attached" when used in reference to Ig-CTF includes attachment of CTF through an ester bond with tyrosine in the immunoglobulin, for example, in SEQ ID NO:45 or 46.

Further "attached" when used in reference to Ig-CTF includes attachment of CTF through an ester bond with a tyrosine in C3b complement binding positions in immunoglobulin, for example SEQ ID NO: 45 or 46, such as at position 144 of SEQ ID NO:45.

Further "attached" when used in reference to Ig-CTF includes attachment of CTF through an ester bond with immunoglobulin, for example, SEQ ID NO: 45 or 46 in the antigen binding region (Fab).

Further "attached" when used in reference to Ig-CTF includes attachment of CTF through an ester or amide bond with a residue in the immunoglobulin, for example, SEQ ID NO: 45 or 46.

Further "attached" can mean other means of bonding two peptides or proteins. Some commonly used cross-linking reagents include: glutaraldehyde which links peptide molecules to the N-terminus of another peptide; carbodiimides (EDC) which attaches a peptide to the C-terminus of another peptide; succinimide esters (e.g. MBS, SMCC) which binds free amino group and Cys residues; benzidine (BDB which links to Tyr residues; periodate which attaches to carbohydrate groups to peptides and isothiocyanates, triazoles and other suitable methods are described generally, for example, in:

L. A. Carpino "1-Hydroxy-7-azabenzotriazole. An efficient peptide coupling additive," J. Am. Chem. Soc. 115 (10): 4397-4398 (1993);

C. Niemeyer, Bio conjugation Protocols: Strategies and Methods

Humana Press, 2004, 344 pp., hard cover;

O'Sullivan, M. J., and Marks, V., Meth. Enzymol., 73, 147-166 (1981).

Harlow, E., and Lane, D.,

Antibodies: A Laboratory Manual, Cold Spring Harbor Laboratory Press (Cold Spring Harbor, N.Y.: 1988) Chapter 9, p. 349.

Further "attached" includes by means of a linker arm such as six carbon straight chain, such as BS-3 which is a homo bifunctional linker or MSH which is a hetero-bifunctional linker. Both of them contain an hexamethylene, —CH6-, group to form a space of 7.5 Angstroms between peptide and carrier protein. The advantage of those linkers is that the distance of a 7.5 Angstrom spacer allows the conjugated peptides to stick out from the surface of the carrier protein, compared with the traditional methods of using glutaldehyde which does not have any spacers. The peptide is therefore more accessible to be antigenic. The covalent bond between the peptide and the carrier protein is very stable, making detachment unlikely during normal immunization procedure.

Further "attached" includes by means of a site of conjugation that can be at the N- or C-terminus or in the middle of the sequence. The point of conjugation can be a sulfhydryl (SH) group or amino group (NH2). A homo-bifunctional linker is to link a peptide and a protein through Lys on both sides. While a hetero-bifunctional linker is to link a peptide through Cys and a protein through Lys or N-terminus.

Further "attached" by other means a coupling reaction that produces a "conjugate" between a CTF of any one of SEQ ID NOs: 1 to 44 and a residue in CTF SEQ ID NOs: 45 to 46 that resembles the native CTF immunoglobulin protein, thus factors such as the location of a residue sequence within a protein will determine where the carrier should be linked. Also, the composition of the immunogen must be considered since different techniques require specific chemistries. Common coupling methods will link carriers to antigens via free amino, carboxylic acid, or sulfhydryl groups.

As used herein, "percent identity" refers to the proportion of the polypeptide sequence that matches the reference polypeptide sequence and can be determined by comparing two optimally aligned sequences over a comparison window, wherein the polypeptide sequence in the comparison window can comprise additions, deletions (i.e., gaps), derivatization, and/or conservative amino acid substitutions as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB, the entire disclosures of which are incorporated herein by reference. See, also, Pearson, et al., Proc. Natl. Acad. Sci. U.S.A., 85:2444-2448, 1988; Atlschul, et al., J. Mol. Biol., 215:403410, 1990; Thompson, et al., Nucleic Acids Res., 22:4673-4680, 1994; Higgins, et al., Meth. Enzymol., 266:383402, 1996; Altschul, et al., Nature Genetics, 3:266-272, 1993; Brutlag, et al., Comp. App. Biosci., 6:237-44, 1990.

As used herein, "derivatization" refers to the process of chemically modifying by techniques such as ubiquitination, labeling, pegylation (i.e, derivatization with polyethylene glycol), and chemical insertion or substitution of amino acids, such as ornithine, which do not normally occur in human proteins.

As used herein, "conservative amino acid substitution" refers to the replacement of one amino acid with another having similar structure and/or chemical properties, such as the replacement of a leucine with an isoleucine or valine, an aspartate with a glutamate, or a threonine with a serine.

As used herein, "polypeptide," "peptide," "chain", and "protein fragment" are used interchangeably herein to refer to a polymer of amino acid residues. The terms include amino acid polymers in which one or more amino acid residues is an artificial chemical mimetic of a corresponding naturally-occurring amino acid, as well as to naturally-occurring amino acid polymers and non-naturally-occurring amino acid polymers.

As used herein, "CTF immunoglobulin" or "Ig-CTF" refers to a CTF peptide attached to immunoglobulin (e.g., IgG, IgA, IgM, IgD, IgE), an immunoglobulin heavy or light chain, or an immunoglobulin fragment (e.g., Fab). For example, the CTF may be attached to immunoglobulin on a gamma heavy chain with at least 75% identity to SEQ ID NO: 45 or a kappa light chain with at least 75% identity to SEQ ID NO: 46. The CTF has at least 75% identity with any one of SEQ ID NOs: 1 to 44. In certain instances, the CTF and immunoglobulin useful in the methods, compositions, and kits do not have the exact sequence as described herein, but is present as a variant form with conservative amino acid substitution and/or derivatization. For example, in some embodiments, the CTF can be substituted in at least 5%, at least 10%, or even at least 25% of its amino acids without having a loss of function. Accordingly, at least some of the amino acids in the peptides of SEQ ID NOs: 1 to SEQ ID NO:46, can be substituted with other amino acids. In particular embodiments, Ig-CTF refers to an isolated polypeptide complex comprising the amino acid sequence of SEQ ID NO: 1 covalently attached to the amino acid sequence of SEQ ID NO: 45 or SEQ ID NO: 46; an isolated polypeptide complex comprising the amino acid sequence of SEQ ID NO: 2 covalently attached to the amino acid sequence of SEQ ID NO: 45 or SEQ ID NO: 46; an isolated polypeptide complex comprising the amino acid sequence of SEQ ID NO: 3 covalently attached to the amino acid sequence of SEQ ID NO: 45 or SEQ ID NO: 46; an isolated polypeptide complex comprising the amino acid sequence of SEQ ID NO: 4 covalently attached to the amino acid sequence of SEQ ID NO: 45 or SEQ ID NO: 46; an isolated polypeptide complex comprising the amino acid sequence of SEQ ID NO: 5 covalently attached to the amino acid sequence of SEQ ID NO: 45 or SEQ ID NO: 46; an isolated polypeptide complex comprising the amino acid sequence of SEQ ID NO: 6 covalently attached to the amino acid sequence of SEQ ID NO: 45 or SEQ ID NO: 46; an isolated polypeptide complex comprising the amino acid sequence of SEQ ID NO: 7 covalently attached to the amino acid sequence of SEQ ID NO: 45 or SEQ ID NO: 46; an isolated polypeptide complex comprising the amino acid sequence of SEQ ID NO: 8 covalently attached to the amino acid sequence of SEQ ID NO: 45 or SEQ ID NO: 46; an isolated polypeptide complex comprising the amino acid sequence of SEQ ID NO: 9 covalently attached to the amino acid sequence of SEQ ID NO: 45 or SEQ ID NO: 46; an isolated polypeptide complex comprising the amino acid sequence of SEQ ID NO: 10 covalently attached to the amino acid sequence of SEQ ID NO: 45 or SEQ ID NO: 46; an isolated polypeptide complex comprising the amino acid sequence of SEQ ID NO: 11 covalently attached to the amino acid sequence of SEQ ID NO: 45 or SEQ ID NO: 46; an isolated polypeptide complex comprising the amino acid sequence of SEQ ID NO: 12 covalently attached to the amino acid sequence of SEQ ID NO: 45 or SEQ ID NO: 46; an isolated polypeptide complex comprising the amino acid sequence of SEQ ID NO: 13 covalently attached to the amino acid sequence of SEQ ID NO: 45 or SEQ ID NO: 46; an isolated polypeptide complex comprising the amino acid sequence of SEQ ID NO: 14 covalently attached to the amino acid sequence of SEQ ID NO: 45 or SEQ ID NO: 46; an isolated polypeptide complex comprising the amino acid sequence of SEQ ID NO: 15 covalently attached to the amino acid sequence of SEQ ID NO: 45 or SEQ ID NO: 46; an isolated polypeptide complex comprising the amino acid sequence of SEQ ID NO: 16 covalently attached to the amino acid sequence of SEQ ID NO: 45 or SEQ ID NO: 46; an isolated polypeptide complex comprising the amino acid sequence of SEQ ID NO: 17 covalently attached to the amino acid sequence of SEQ ID NO: 45 or SEQ ID NO: 46; an isolated polypeptide complex comprising the amino acid sequence of SEQ ID NO: 18 covalently attached to the amino acid sequence of SEQ ID NO: 45 or SEQ ID NO: 46; an isolated polypeptide complex comprising the amino acid sequence of SEQ ID NO: 19 covalently attached to the amino acid sequence of SEQ ID NO: 45 or SEQ ID NO: 46; an isolated polypeptide complex comprising the amino acid sequence of SEQ ID NO: 20 covalently attached to the amino acid sequence of SEQ ID NO: 45 or SEQ ID NO: 46; an isolated polypeptide complex comprising the amino acid sequence of SEQ ID NO: 21 covalently attached to the amino acid sequence of SEQ ID NO: 45 or SEQ ID NO: 46; an isolated polypeptide complex comprising the amino acid sequence of SEQ ID NO: 22 covalently attached to the amino acid sequence of SEQ ID NO: 45 or SEQ ID NO: 46; an isolated polypeptide complex comprising the amino acid sequence of SEQ ID NO: 23 covalently attached to the amino acid sequence of SEQ ID NO: 45 or SEQ ID NO: 46; an isolated polypeptide complex comprising the amino acid sequence of SEQ ID NO: 24 covalently attached to the amino acid sequence of SEQ ID NO: 45 or SEQ ID NO: 46; an isolated polypeptide complex comprising the amino acid sequence of SEQ ID NO: 25 covalently attached to the amino acid sequence of SEQ ID NO: 45 or SEQ ID NO: 46; an isolated polypeptide complex comprising the amino acid sequence of SEQ ID NO: 26 covalently attached to the amino acid sequence of SEQ ID NO: 45 or SEQ ID NO: 46; an isolated polypeptide complex comprising the amino acid sequence of SEQ ID NO: 27 covalently attached to the amino acid sequence of SEQ ID NO: 45 or SEQ ID NO: 46; an isolated polypeptide complex comprising the amino acid sequence of SEQ ID NO: 28 covalently attached to the amino acid sequence of SEQ ID NO: 45 or SEQ ID NO: 46; an isolated polypeptide complex comprising the amino acid sequence of SEQ ID NO: 29 covalently attached to the amino acid sequence of SEQ ID NO: 45 or SEQ ID NO: 46; an isolated polypeptide complex comprising the amino acid sequence of SEQ ID NO: 30 covalently attached to the amino acid sequence of SEQ ID NO: 45 or SEQ ID NO: 46; an isolated polypeptide complex comprising the amino acid sequence of SEQ ID NO: 31 covalently attached to the amino acid sequence of SEQ ID NO: 45 or SEQ ID NO: 46; an isolated polypeptide complex comprising the amino acid sequence of SEQ ID NO: 32 covalently attached to the amino acid sequence of SEQ ID NO: 45 or SEQ ID NO: 46; an isolated polypeptide complex comprising the amino acid sequence of SEQ ID NO: 33 covalently attached to the amino acid sequence of SEQ ID NO: 45 or SEQ ID NO: 46; an isolated polypeptide complex comprising the amino acid sequence of SEQ ID NO: 34 covalently attached to the amino acid sequence of SEQ ID NO: 45 or SEQ ID NO: 46; an isolated polypeptide complex comprising the amino acid sequence of SEQ ID NO: 35 covalently attached to the amino acid sequence of SEQ ID NO: 45 or SEQ ID NO: 46; an isolated polypeptide complex comprising the amino acid sequence of SEQ ID NO: 36 covalently attached to the amino acid sequence of SEQ ID NO: 45 or SEQ ID NO: 46; an isolated polypeptide complex comprising the amino acid sequence of SEQ ID NO: 37 covalently attached to the amino acid sequence of SEQ ID NO: 45 or SEQ ID NO: 46; an isolated polypeptide complex comprising the amino acid sequence of SEQ ID NO: 38 covalently attached to the amino acid sequence of SEQ ID NO: 45 or SEQ ID NO: 46; an isolated polypeptide complex comprising the amino acid sequence of SEQ ID NO: 39 covalently attached to the amino acid sequence of SEQ ID NO: 45 or SEQ ID NO: 46; an isolated polypeptide complex comprising the amino acid sequence of SEQ ID NO: 40 covalently attached to the amino acid sequence of SEQ ID NO: 45 or SEQ ID NO: 46; an isolated polypeptide complex comprising the amino acid sequence of SEQ ID NO: 41 covalently attached to the amino acid sequence of SEQ ID NO: 45 or SEQ ID NO: 46; an isolated polypeptide complex comprising the amino acid sequence of SEQ ID NO: 42 covalently attached to the amino acid sequence of SEQ ID NO: 45 or SEQ ID NO: 46; an isolated polypeptide complex comprising the amino acid sequence of SEQ ID NO: 43 covalently attached to the amino acid sequence of SEQ ID NO: 45 or SEQ ID NO: 46; an isolated polypeptide complex comprising the amino acid sequence of SEQ ID NO: 44 covalently attached to the amino acid sequence of SEQ ID NO: 45 or SEQ ID NO: 46; or any combination thereof.

Immunoglobulins useful in the invention may be produced recombinantly, by monoclonal hydridomas, or isolated biologically from their natural environment, e.g., from cells, animals or humans. For example, antibody-producing cells are fused with cells that grow continuously in culture to form hybridomas. A single hybridoma produces only one antibody. A single hybridoma divides to produce a large population of 'clones' all making the same "monoclonal" antibody. Living hybridomas can be frozen indefinitely in liquid nitrogen. Preferred antibodies that preferentially bind CTF either as free CTF or as the CTF portion of Ig-CTF are provided. In particular embodiments are provided antibodies that preferentially bind an isolated polypeptide comprising the amino acid sequence of SEQ ID NO: 49 (Antigen used to make 461-4H11); an isolated polypeptide comprising the amino acid sequence of SEQ ID NO:50 (Antigen used to make 444-1D12); an isolated polypeptide comprising the amino acid sequence of SEQ ID NO: 51 (Antigen used to make 515-4D6); or an isolated polypeptide comprising the amino acid sequence of SEQ ID NO: 52 (Antigen used to make 510-6B6).

As used herein, "antigen of CTF immunoglobulin" is defined as a molecule, substance, protein or peptide that is recognized by or bound to the CTF immunoglobulin and is isolated biologically from cells, animals, and humans producing CTF immunoglobulin. Further, this "antigen of CTF immunoglobulin" would be made by all species producing CTF immunoglobulin and can be antigens on cells, in tissues or free in bodily fluids such as urine, blood, cerebrospinal fluid (CSF) or interstitial fluid.

The "CTF" and "antigen to CTF immunoglobulin" may be isolated from biological material or prepared recombinantly, or preferably as peptides by synthetic conventional methods of synthesis in liquid-phase or solid-phase, using manual or automated techniques. Suitable methods are described generally, for example, in:

Atherton, E. and Sheppard, R. C., Solid Phase peptide synthesis: a practical approach. Oxford, England: IRL Press (1989);

Stewart, J. M. and Young, J. D., Solid phase peptide synthesis, 2nd edition, Rockford: Pierce Chemical Company, 91 (1984);

R. B. Merrifield, "Solid Phase Peptide Synthesis. I. The Synthesis of a Tetrapeptide," J. Am. Chem. Soc. 85 (14): 2149-2154 (1963); and L. A. Carpino "1-Hydroxy-7-azabenzotriazole. An efficient peptide coupling additive," J. Am. Chem. Soc. 115 (10): 4397-4398 (1993), which are incorporated herein by reference. Additionally, any portion of the amino acid sequence of the peptides can be altered during direct synthesis and/or combined using chemical methods with sequences or with other proteins to produce a variant peptide.

As used herein, "preferentially binds" means that an antibody binds a target, but may also bind a limited number of other molecules. "Preferential binding" when used in the context of antibodies, or antibody fragments, represents binding via domains encoded by immunoglobulin genes or fragments of immunoglobulin genes to one or more epitopes of a protein of interest, without favoring binding to other molecules in a sample containing a mixed population of molecules.

Preferably, the peptides are prepared by conventional solid-phase peptide synthesis methodology. Standard synthesis protocols based on Fmoc chemistry may be used. After synthesis, the crude peptides are cleaved from the solid support and side-chain protecting groups are removed. The crude peptides can be purified, for example, by preparative high performance liquid chromatography, such as C18 reverse-phase HPLC. The purified peptide can be further desalted by HPLC and lyophilized to dry form. Preferably, the peptides are stored in sealed containers under nitrogen.

All forms of the peptides of SEQ ID NOs:1 to NO:46, including free acid, free base, zwitterionic form, isomorphic crystalline forms, all chiral, enantiomeric, racemic forms, hydrates, solvates, salts and acid salt hydrates, are contemplated to be within the scope of the subject matter described herein. The free acid and the sodium, potassium, and calcium salts are the preferred forms.

In accordance with the subject matter described herein, the peptides of SEQ ID NOs:1 to NO:46 may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., Protective Groups in Organic Synthesis 2d. Ed., Wiley & Sons, 1991.

As used herein, "treating" refers to the preventative, curative, and palliative treatment of a condition, and minimally requires a palliative effect. The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

The term "progression," as used in the context of progression of a condition includes the change of the condition from a less severe to a more severe or advanced state.

The term "regression," as used in the context of regression of a condition, includes the change of a the condition from a more severe to a less severe or advanced state.

The term "stable" as used in the context of stable condition, is intended to describe a disease condition that is not, or has not, changed significantly enough over a clinically relevant period of time to be considered a progressing condition or a regressing condition.

As used herein, the terms "subject" and "patient" are used interchangeably to refer to an animal, including a mammal, preferably a human.

As used herein, "healthy" refers to a patient that is not currently suffering from a condition or disease and includes a patient who is predisposed to suffering a condition.

As used herein, "diagnosis" or "diagnose" refers to identification of patients with a condition, such as insulin resistance, abnormal cell growth, or liver disease. "Diagnosis" or "diagnose" also refers to identification of patients in need of treatment. In some embodiments, the insulin resistance is associated with impaired glucose tolerance, prediabetes, type 1 diabetes, type 2 diabetes, type 3 diabetes, juvenile diabetes or gestational diabetes. In some embodiments, the abnormal cell growth is cancer, such as for example, breast cancer, metastatic cancer, pancreatic cancer, or hepatocellular carcinoma. In some embodiments, the liver disease is autoimmune hepatitis, nonalcoholic steatohepatitis (NASH), or alcoholic hepatitis.

As used herein, "diabetes" refers to diabetes mellitus, a chronic hyperglycemia due to defective insulin secretion and/or action. The World Health Organization recognizes three main forms of diabetes mellitus: type I, type II, type 3 diabetes, juvenile diabetes and gestational diabetes. While all forms are due to the beta cells of the pancreas being unable to produce sufficient insulin to prevent hyperglycemia, the causes are different. Type I diabetes is usually due to autoimmune destruction of the pancreatic beta cells. Type II diabetes is characterized by insulin resistance in target tissues, which creates a need for abnormally high amounts of insulin and diabetes develops when the beta cells cannot meet this demand. Gestational diabetes is similar to type II diabetes in that it involves insulin resistance; the hormones of pregnancy can cause insulin resistance in women genetically predisposed to developing this condition. Gestational diabetes typically resolves with delivery of the child, however types I and II diabetes are chronic conditions. All types are treatable with insulin. Type I diabetes, in which insulin is not secreted by the pancreas, is directly treatable only with injected or inhaled insulin, although dietary and other lifestyle adjustments are part of management. Type II may be managed with a combination of dietary treatment, tablets and injections and, frequently, insulin supplementation.

As used herein, "cardiovascular disease" refers to any disease that affects the heart and blood vessels, including diseases related to atherosclerosis (arterial disease) that can cause heart attacks and certain types of strokes.

Figure 2:
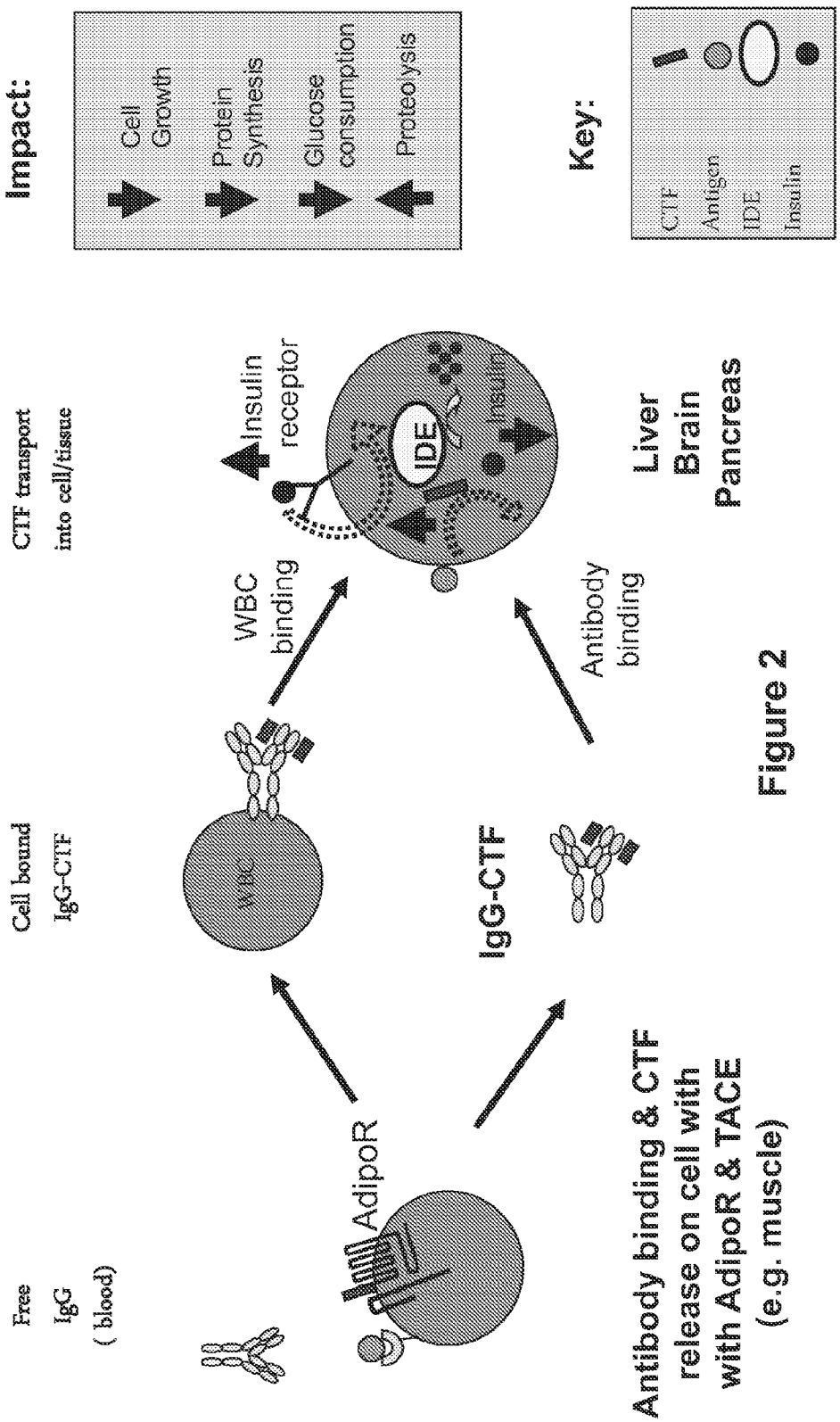
FIG. 2 illustrates the proposed pathology of Ig-CTF autoimmunity. In abnormal patients, tumor necrosis factor-α-converting enzyme (TACE) cleaves the CTF from adiponectin receptors which adiponectin blocks. This cleavage allows the covalent linkage of CTF to immunoglobulins attracted to the region surrounding the adiponectin receptors. The immunoglobulins are either on cells or freely circulating. Once covalently linked, the Ig-CTF is absorbed into tissues. This absorption increases the intercellular concentration of CTF. This desensitizes the cells to insulin as CTF inhibits the insulin degradation enzyme (IDE) in the liver. This prevents IDE from degrading intercellular insulin which causes a weaker insulin receptor response.

As used herein, "insulin resistance" refers to decrease in an individual in the biological action of insulin in vivo as assessed by the rate of disposal of glucose from the bloodstream (e.g., into insulin-sensitive tissue, such as muscle, fat, and liver). Insulin resistance occurs in patients with diabetes, cardiovascular disease, abnormal adipocyte activity, and metabolic syndrome. For certain embodiments, "insulin resistance" refers to CTF inhibition of insulin degradation enzyme (IDE) raising intercellular insulin and reducing insulin receptor response (FIG. 1). "Insulin resistance" also refers to inhibition of insulin degradation enzyme preventing the degradation of amyloid beta leading deposits associated with Alzheimer's disease. In further embodiments, "insulin resistance" resistance by antigens on normal cells being targeted by CTF immunoglobulin leading to active transport of CTF immunoglobulin from the plasma into cells for utilization of CTF as an inhibitor of IDE (FIG. 2).

As used herein, "abnormal cell growth" refers to increased cell growth in an individual with cancer or inflammatory disease as assessed by cell proliferation and abnormal cell growth. In some embodiments, "abnormal cell growth" is decreased by "insulin resistance" due to reduced insulin receptor response and patients with "abnormal cell growth" have levels of CTF immunoglobulin. For other embodiments, "abnormal cell growth" occurs when CTF inhibits ADAM-17 enzyme, and is associated with increased TNF-alpha, and HER2 neu in the patient. For other embodiments, CTF immunoglobulin is a mechanism to inhibit cell growth in abnormal cells (such as pre cancerous or aged cells where growth is slowed by insulin resistance and abnormal cells targeted by antigens that differentiate an abnormal from normal cell.

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof, including acid addition salts and base addition salts.

Examples of pharmaceutically acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "effective amount" refers to an amount of the active ingredient as described herein that may be effective to prevent, reduce or eliminate the symptoms or condition and, with respect to this invention, including to treat insulin resistance and abnormal cell growth.

In general, the effective amount of the CTF fragments of the invention, ranges from about 0.25 mg per kg patient weight to about 200 mg per kg patient weight, preferably about 25 mg per kg patient weight to about 175 mg per kg patient weight, and more preferably about 30 mg per kg patient weight to about 150 mg per kg patient weight (and all combinations and subcombinations therein).

The useful compositions, dosage forms, and kits of CTF immunoglobulin have also been discovered, Thus provided herein are pharmaceutical compositions of Ig-CTF. In some embodiments, the Ig-CTF is in the form of a pharmaceutical acceptable salts. In some embodiments, the pharmaceutical composition of Ig_CTF comprises Ig-CTF and at least one pharmaceutically acceptable carrier. In preferred embodiments, the pharmaceutical composition of Ig-CTF is in an injectable, parenteral, infusable or inhalable dosage form. In some embodiments, kits comprising the Ig-CTF or a pharmaceutical composition thereof and instructions for administering the same are provided.

In certain embodiments of the invention, the peptide or pharmaceutically acceptable salt thereof is administered via a parenteral route. In certain preferred embodiments, the peptide or pharmaceutically-acceptable salt thereof is administered via injection. In other preferred embodiments, the peptide or pharmaceutically-acceptable salt thereof is administered via infusion. In yet other preferred embodiments, the peptide or pharmaceutically-acceptable salt thereof is administered via inhalation.

Pharmaceutical kits useful in, for example, the treatment of insulin resistance, liver disease, or abnormal cell growth, comprise an effective amount of any of the peptides of SEQ ID NOs:1 to NO:46 or pharmaceutically acceptable salts thereof in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. Such kits may further include, if desired, one or more of various conventional pharmaceutical kit components, such as for example, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

By "reporter molecule", as used in the present specification, is meant a molecule which, by its chemical nature, produces an analytically identifiable signal which allows the detection of antigen-bound antibody. Detection can be either qualitative or quantitative. The most commonly used reporter molecule in this type of assay are either colored latex particles, metal particles, enzymes, fluorophores or radionuclide containing molecules (i.e. radioisotopes)

The embodiments described herein are not limited to particular methods, reagents, compounds, compositions or biological systems, which can, of course, vary.

Detection and Monitoring of Ig-CTF

The present invention provides methods of detecting Ig-CTF. In one embodiment, a biological sample derived from a subject of a first species is exposed to a first antibody of a second species that preferentially binds the first species' Ig-CTF or an antigen binding fragment of that first antibody and this forms a mixture. After this step, an optional washing step can be performed. This mixture is then exposed to a second antibody or an antigen-binding fragment of a third species that preferentially binds the first species' Ig. After this step, an optional washing step can be performed. Then the Ig-CTF present in the sample is detected. There are many different assay platforms that could be used to detect the Ig-CTF.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized by the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The Ig-CTF can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequence of SEQ ID NOs: 1 to 22. Examples of amino acid sequences of AdipoR2 include the amino acid sequence of the amino acid sequence of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid or histological preparations. Because of their ease of access and handling, blood and plasma may be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammals. A preferred embodiment would be where the mammals are humans. However, other mammals, including zoo, research, and domestic animals (pets) such as a mouse, rat, guinea pig, hamster, dog, cat, sheep, cow, horse, donkey, mule, or pig may be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma ($\gamma$) heavy chains, and kappa ($\kappa$) or lambda ($\lambda$) light chains. IgA is made up of alpha ($\alpha$) heavy chains and kappa ($\kappa$) or lambda ($\lambda$) light chains. IgM is made up of mu ($\mu$) heavy chains and kappa ($\kappa$) or lambda ($\lambda$) light chains. IgD is made up of delta ($\delta$) heavy chains and kappa ($\kappa$) or lambda ($\lambda$) light chains. IgE is made up of epsilon ($\epsilon$) heavy chains and kappa ($\kappa$) or lambda ($\lambda$) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

In another embodiment, the first species, the second species, and the third species are not the same species.

In some embodiments, it is desirable to monitor the levels of Ig-CTF and not just detect it. Also provided are methods of monitoring the level of Ig-CTF. In one embodiment, a biological sample obtained from a subject of a first species is exposed to a first antibody of a second species that preferentially binds the first species' Ig-CTF or an antigen binding fragment of that first antibody and this forms a mixture. After this step, an optional washing step can be performed. This mixture is then exposed to a second antibody or an antigen-binding fragment of a third species that preferentially binds the first species' Ig. After this step, an optional washing step can be performed. Then the Ig-CTF present in the sample is quantified and then the amount of Ig-CTF present in the sample is compared to a known standard, or to the amount of Ig-CTF present in a biological sample obtained from the subject at an earlier point in time. In another embodiment, this comparison can show whether the Ig-CTF has increased, decreased or stabilized over time. There are many different assay platforms that could be used to monitor the levels of Ig-CTF.

In certain embodiments, the level of expression, including the presence or absence of at least one soluble Ig-CTF, is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized by the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be monitored by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequence of the amino acid sequences of SEQ ID NOs: 23, to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluids or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. In a preferred embodiment, the sample is obtained from a human. However, other mammals, including zoo, research, and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7(clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

In another embodiment, the first species, the second species, and the third species are not the same species.

The present inventions also provide kits for detecting the presence of Ig-CTF in a biological sample, comprising a first isolated antibody that preferentially binds Ig CTF produced by the cell line deposited with the ATCC having accession number 444-1D12.1H7 (mAb 444-1D12), a first isolated antibody that preferentially binds CTF produced by the cell line deposited with the ATCC having accession number 510-6B6.1G1 (mAb-510-6B6); and/or a first isolated antibody that preferentially binds CTF produced by the cell line deposited with the ATCC having accession number 515-4D6.1B10 (mAb-515-4D6), a second antibody or antigen-binding fragment that preferentially binds human Ig and instructions for use of the first antibody or antigen-binding fragment and the second antibody or antigen-binding fragment together with packaging for the same.

In a preferred embodiment, the Ig in Ig-CTF, is IgG. In another preferred embodiment, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein-or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In an embodiment of the invention, the kit also contains a vessel for containing the first antibody or antigen-binding fragment. For example, the vessel can be a 1.5 mL tube, 5 mL tube, 15 mL tube, 25 mL tube or 50 mL tube. These tubes can be made out of materials such as polycarbonate, plastic or glass. In another embodiment of the invention, the kit also contains a vessel for containing the secons antibody or antigen-binding fragment when not in use. For example, the vessel can be a 1.5 mL tube, 5 mL tube, 15 mL tube, 25 mL tube or 50 mL tube. These tubes can be made out of materials such as polycarbonate, plastic or glass.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

Using Ig-CTF in Diagnosing, Treating and Monitoring Insulin Resistance

An embodiment of the invention provided is a method for diagnosing insulin resistance in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with insulin resistance.

As examples, insulin resistance may be associated with impaired glucose tolerance, prediabetes, type 1 diabetes, type 2 diabetes, type 3 diabetes, juvenile diabetes, gestational diabetes, or nonalcoholic steatohepatitis (NASH).

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiponectin receptor 1 (adiporeceptor 1; "AdipoR1") and adiponectin receptor 2 (adiporeceptor 2; "AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23-44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods described herein, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluids or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. A preferred embodiment would be where the mammal is human. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone 510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma ($\gamma$) heavy chains, and kappa ($\kappa$) or lambda ($\lambda$) light chains. IgA is made up of alpha ($\alpha$) heavy chains and kappa ($\kappa$) or lambda ($\lambda$) light chains. IgM is made up of mu ($\mu$) heavy chains and kappa ($\kappa$) or lambda ($\lambda$) light chains. IgD is made up of delta ($\delta$) heavy chains and kappa ($\kappa$) or lambda ($\lambda$) light chains. IgE is made up of epsilon ($\epsilon$) heavy chains and kappa ($\kappa$) or lambda ($\lambda$) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled $\alpha 2$-MG-, HA-, TIMP-1- or YKL-40-specific binding agents such as anti$\alpha 2$-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), $\beta$-galactosidase or urease can be linked, for example, to an anti-adiponectin receptor C terminal fragment or to a secondary antibody for use in a method of the invention. A horse-radish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Another embodiment of the invention provided is a method for treating insulin resistance in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with insulin resistance and administering to the subject, or prescribing, a treatment for insulin resistance.

As examples, insulin resistance may be associated with impaired glucose tolerance, prediabetes, type 1 diabetes, type 2 diabetes, type 3 diabetes, juvenile diabetes, gestational diabetes, or nonalcoholic steatohepatitis (NASH).

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammals. A preferred embodiment would be where the mammals are humans. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several sub-units. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Examples of treatments for insulin resistance include reducing the need for insulin, increasing the sensitivity of cells to the action of insulin or supplementing insulin. Reducing the need for insulin can occur, for example, through changes in diet. Increasing the sensitivity of cells to the action of insulin can occur, for example, by taking medications such as Glucophage, pioglitazone and rosiglitazone. Supplementing insulin can occur, for example, by introducing insulin into the subject.

Another embodiment of the invention provided is a method for monitoring insulin resistance in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. The quantity of Ig-CTF in the sample is then compared to a either a known standard or the amount of Ig-CTF present in a biological sample obtained from the subject at an earlier point in time. It can then be determined whether the subject's level of Ig-CTF is indicative of progression, regression, or stabilization of insulin resistance.

As examples, insulin resistance may be associated with impaired glucose tolerance, prediabetes, type 1 diabetes, type 2 diabetes, type 3 diabetes, juvenile diabetes, gestational diabetes, or nonalcoholic steatohepatitis (NASH).

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods described herein, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammals. A preferred embodiment would be where the mammals are humans. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma ($\gamma$) heavy chains, and kappa ($\kappa$) or lambda ($\lambda$) light chains. IgA is made up of alpha ($\alpha$) heavy chains and kappa ($\kappa$) or lambda ($\lambda$) light chains. IgM is made up of mu ($\mu$) heavy chains and kappa ($\kappa$) or lambda ($\lambda$) light chains. IgD is made up of delta ($\delta$) heavy chains and kappa ($\kappa$) or lambda ($\lambda$) light chains. IgE is made up of epsilon ($\epsilon$) heavy chains and kappa ($\kappa$) or lambda ($\lambda$) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled $\alpha$2-MG-, HA-, TIMP-1- or YKL-40-specific binding agents such as anti$\alpha$2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity.

When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

In another embodiment of the inventions, the known standard may be the Ig-CTF level of subjects being identified as having normal insulin sensitivity. In another embodiment of the invention, the known standard may be the Ig-CTF level of subjects being identified as insulin-resistant. In another embodiment of the invention, the known standard may be the Ig-CTF level of subjects being identified as diabetic. In another embodiment of the invention, the biological sample recited in step is obtained from said subject following treatment for insulin resistance or diabetes or the biological sample is obtained from the subject at an earlier point in time is obtained from the subject following treatment for insulin resistance or diabetes.

Using Ig-CTF in Diagnosing, Treating and Monitoring Cancer

Another embodiment provided herein are methods for diagnosing cancer in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with cancer.

As examples, the cancer may be breast cancer, metastatic cancer, hepatocellular carcinoma, or pancreatic cancer.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs:

23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods described herein, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. A preferred embodiment would be where the mammal is human. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Another embodiment of the invention provided is a method for treating cancer in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with cancer and administering to the subject, or prescribing, a treatment for cancer.

As examples, the cancer may be breast cancer, metastatic cancer, hepatocellular carcinoma, or pancreatic cancer.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. A preferred embodiment would be where the mammal is human. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma ($\gamma$) heavy chains, and kappa ($\kappa$) or lambda ($\lambda$) light chains. IgA is made up of alpha ($\alpha$) heavy chains and kappa ($\kappa$) or lambda ($\lambda$) light chains. IgM is made up of mu ($\mu$) heavy chains and kappa ($\kappa$)

or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein-or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Examples of cancer treatments include surgery, hormone therapy, radiation, chemotherapy, immunotherapy, targeted therapy, and combinations thereof. Examples of hormone therapy drugs include aromatase inhibitors and luteinizing hormone-releasing hormone analogs and inhibitors. Examples of radiation treatments include the related techniques of conformal proton beam radiation therapy, stereotactic radiosurgery, stereotactic radiation therapy, intraoperative radiation therapy, chemical modifiers, and radio sensitizers. Examples of chemotherapy drugs include aminopterin, cisplatin, methotrexate, doxorubicin, daunorubicin and others alone and in combinations. Examples of cancer treatments also include biological response modifier (BRM) therapy, biologic therapy, biotherapy, and immunotherapy. Examples of BRMs include interferons, interleukins, and other cytokines and antibodies such as rituximab and trastuzumab and even cancer vaccines such as Sipuleucel-T. Other examples of cancer therapies include targeted therapies like growth signal inhibitors such as trastuzumab, gefitinib, imatinib, centuximab, dasatinib and nilotinib. Another type of targeted therapy includes angiogenesis inhibitors such as bevacizumab that inhibit cancers from increasing surrounding vasculature and blood supply. A final type of targeted therapy includes apoptosis-inducing drugs that are able to induce direct cancer cell death.

Another embodiment of the invention provided is a method for monitoring cancer in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. The quantity of Ig-CTF in the sample is then compared to a either a known standard or the amount of Ig-CTF present in a biological sample obtained from the subject at an earlier point in time. It can then be determined whether the subject's level of Ig-CTF is indicative of progression, regression, or stabilization of cancer.

As examples, the cancer may be breast cancer, metastatic cancer, hepatocellular carcinoma, or pancreatic cancer.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporeceptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammals. A preferred embodiment would be where the mammals are humans. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

In another embodiment of the inventions, the known standard may be the Ig-CTF level of subjects being identified as free of cancer. In another embodiment of the invention, the known standard may be the Ig-CTF level of subjects being identified as having cancer. In another embodiment of the invention, the biological sample recited in step a. is obtained from the subject following treatment for cancer or the biological sample is obtained from the subject at an earlier point in time is obtained from the subject following treatment for cancer.

Using Ig-CTF in Diagnosing, Treating and Monitoring Liver Disease

An embodiment of the invention provided is a method for diagnosing liver disease in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with liver disease.

Examples of liver disease includes autoimmune hepatitis, nonalcoholic steatohepatitis (NASH), or alcoholic hepatitis.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluids, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. A preferred embodiment would be where the mammal is human. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking, covalently binding, or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}I$, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Another embodiment of the invention provided is a method for treating liver disease in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. Finally, the amount of Ig-CTF present in the sample is compared to a known standard and it is determined whether the amount of Ig-CTF in the sample falls within the level of Ig-CTF associated with cancer and administering to the subject, or prescribing, a treatment for liver disease.

Examples of liver disease includes autoimmune hepatitis, nonalcoholic steatohepatitis (NASH), or alcoholic hepatitis.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR2 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluids or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammal. A preferred embodiment would be where the mammal is human. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma ($\gamma$) heavy chains, and kappa ($\kappa$) or lambda ($\lambda$) light chains. IgA is made up of alpha ($\alpha$) heavy chains and kappa ($\kappa$) or lambda ($\lambda$) light chains. IgM is made up of mu ($\mu$) heavy chains and kappa ($\kappa$) or lambda ($\lambda$) light chains. IgD is made up of delta ($\delta$) heavy chains and kappa ($\kappa$) or lambda ($\lambda$) light chains. IgE is made up of epsilon ($\epsilon$) heavy chains and kappa ($\kappa$) or lambda ($\lambda$) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, a chemiluminescent label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

Examples of treatments of liver disease include medications, outpatient procedures, surgery and liver transplants.

Another embodiment of the invention provided is a method for monitoring liver disease in a subject. In one embodiment, a biological sample derived from a subject is exposed to a first antibody of a second species that preferentially binds the first species' Ig-CTF or an antigen-binding fragment of that first antibody and this forms a mixture. After this step, an optional washing step can be performed. This mixture is then exposed to a second antibody or antigen-binding fragment of a third species that preferentially binds the first species' Ig. After this step, an optional washing step can be performed. Then the Ig-CTF present in the sample is quantified. The quantity of Ig-CTF in the sample is then compared to a either a known standard or the amount of Ig-CTF present in a biological sample obtained from the subject at an earlier point in time. It can then be determined whether the subject's level of Ig-CTF is indicative of progression, regression, or stabilization of liver disease.

In certain embodiments, the level of expression, including the presence or absence of at least one soluble Ig-CTF is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. For example, provided herein are the specific CTF targets of the deposited antibodies: SEQ ID NO: 49, HVLVVAAAFVHFCYS, SEQ ID NO: 50, HFYGVSNLQEFRYGLEGGCTDDSLL, SEQ ID NO: 51, GGCTDDTLL and SEQ ID NO: 52, GGCSEEDAL. In certain preferred embodiments, the immunointeractive molecule will be an antibody. For example, these sequences are recognized to the deposited antibodies: clone 461-4H11, clone 444-1D12, clone 515-4D65 and clone 510-6B6 respectively. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example enzyme immunoassay, radioimmunoassay, enzyme-linked immunosorbent assays (ELISA), immuno-tubimetric, immunonephrometric, magnetic immuno particle separation, immunochromatography, immuno-microfludic, immuno-centrifugal, diffusion-based Ouchterlony, rocket gel immunoelectrophoresis or in situ immunoassays can be readily adapted to the present purpose.

Immunoassays are useful in the quantification of at least one Ig-CTF of the adiponectin receptor in a test sample, in particular to determine whether the level of the at least one Ig-CTF is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

Other examples of detecting Ig-CTF include quantitative western blotting, immunohistochemistry, protein biochips, mass spectrometry and others.

The CTF immunoglobulin can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Ig-CTF itself can comprise a C-terminal fragment of adiporeceptor covalently attached to an immunoglobulin. The term "adiporeceptor" includes adiporecptor 1 ("AdipoR1") and adiporeceptor 2 ("AdipoR2"). Examples of amino acid sequences of AdipoR1 include the amino acid sequences of SEQ ID NOs: 1 to 22. Examples of amino acid sequences of AdipoR1 include the amino acid sequences of SEQ ID NOs: 23 to 44. In the methods of the present invention, one or more of the (i.e., at least one) Ig-CTF can be detected. For example, any one or combination of Ig-CTF wherein the CTF is one of the fragments represented by the amino acid sequences of SEQ ID NO: 1 to SEQ ID NO: 44 can be detected.

In the methods of the present inventions, the biological sample can come from a number of sources. For example, the biological sample can be derived from urine, blood, serum plasma, saliva, ascites, circulating cells, circulating tumor cells, cells that are not tissue associated, tissues, surgically resected tumor tissue, biopsies, fine needle aspiration samples, cerebrospinal fluid, white blood cells, interstitial fluid, or histological preparations. Because of their ease of access and handling, blood and plasma can be particularly useful sources of the biological sample.

In some cases, a preservative may help stabilize the biological samples for storage while being refrigerated or frozen. Examples of suitable preservatives include fluoride, heparin, or EDTA.

In other embodiments, the tissue is liver, pancreas, lymph node, adipose, muscle, or brain. An example of a method to detect Ig-CTF in these tissues is immunohistochemistry (tissue staining).

The biological samples can be derived from any mammals. A preferred embodiment would be where the mammals are humans. However, other mammals, including zoo, research and domestic animals (pets) such as a mouse, rat, guinea pig, hamster, dog, cat, sheep, cow, horse, donkey, mule, or pig would also be potential sources of biological samples.

In other embodiments of the invention, antibodies are provided that could be used as the first antibody for the method. For example, an isolated antibody that preferentially binds Ig-CTF produced by the cell line deposited with the ATCC having accession number 444-1D12.1H7 (clone 444-1D12), an isolated antibody that preferentially binds CTF produced by the cell line deposited with the ATCC having accession number 510-6B6.1G1 (clone-510-6B6); or an isolated antibody that preferentially binds CTF produced by the cell line deposited with the ATCC having accession number 515-4D6.1B10 (clone-515-4D6). The antigens and methodology used to prepare these antibodies is explained fully in Example 12.

In some cases, the first antibody or antigen-binding fragment is bound to a solid support. The solid support is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs, plates or microplates, or any other surface suitable for conducting an immunoassay. The binding processes are well-known in the art and generally consist of cross-linking covalently binding or physically adsorbing the molecule to the insoluble carrier. In one embodiment, the solid support is an EIA/RIA plate.

In the Ig-CTF, the Ig can be the immunoglobulin isotypes IgG, IgA, IgM, IgD, or IgE. A preferred example of an Ig in Ig-CTF, is IgG Immunoglobulins are made from several subunits. For example, IgG is made up of a gamma (γ) heavy chains, and kappa (κ) or lambda (λ) light chains. IgA is made up of alpha (α) heavy chains and kappa (κ) or lambda (λ) light chains. IgM is made up of mu (μ) heavy chains and kappa (κ) or lambda (λ) light chains. IgD is made up of delta (δ) heavy chains and kappa (κ) or lambda (λ) light chains. IgE is made up of epsilon (ε) heavy chains and kappa (κ) or lambda (λ) light chains. The Ig of Ig-CTF can also be a subunit of one of the isotypes of immunoglobulin. For example, the Ig can be a Kappa light chain of IgG, IgM, or IgA or the Ig can be a Gamma heavy chain of IgG. Alternatively, the Ig can be an antigen binding region (Fab).

In some embodiments, the second antibody or antigen-binding fragment is detectably labeled. Examples of detectable labels include a radiolabel, a fluorescent label, an epitope tag, biotin, a chromophore label, an electrochemiluminescence (ECL) label, or an enzyme. Radiolabels include $^{125}$I, which can be attached to an antibody (Harlow and Lane, supra, 1988). Useful fluorescent labels include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as antiα2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.). Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm.

In other embodiments, free CTF is not detected because of the design of the assays.

In another embodiment of the inventions, the known standard may be the Ig-CTF level of subjects being identified as normal. In another embodiment of the invention, the known standard may be the Ig-CTF level of subjects being identified as having liver disease. In another embodiment of the invention, the biological sample recited in step a. is obtained from the subject following treatment for liver disease or the biological sample is obtained from the subject at an earlier point in time is obtained from the subject following treatment for liver disease.

The present invention is further defined in the following Examples, in which all parts and percentages are by weight, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Detection of CTF Immunoglobulin in Blood, Tissue and Cells

Western blot analyses were run on human plasma, pancreas, adipose, liver and muscles tissue, as well as myocytes and epithelial cell culture homogenates according to the following methods and variations thereof.

Samples and homogenates with protein concentration of about 20 ug/ml were boiled in water for 5 minutes in buffer with SDS and chilled on ice to denature the protein. The sample was then centrifuged to remove precipitate and was boiled sample 1:1 with BioRad Laemmli buffer with 5% beta-mercaptoethanol to break the disulfide bonds. The treated samples were loaded onto the 12% or 10% Ready Gel (Biorad) and SDS-PAGE gel was run in Tris, glycine, SDS buffer (BioRad) at 110V (BioRad PROTEAN® Tetra Cel) for 1-1.5 hours until the bromophenol blue reached the bottom of the gel. Gel plates were disassembled, soaked in transfer buffer and the gels were transferred to 0.2 um nitrocellulose paper at 30V in a 4° C. chamber overnight.

After the protein transfer, the nitrocellulose was rinsed and washed with TTBS buffer (20 mM Tris, 500 mM NaCl, pH 7.4, 0.1% Tween®-20). The membrane was then blocked with 5% BSA in TTBS at room temperature with gentle agitation. The blocking buffer was then removed and the membrane was incubated with antibodies conjugated to alkaline phosphatase or horse radish peroxidase. For AdipoR1 CTF, the mAb 444-1D12 conjugated to alkaline phosphatase was used (2.5 mg/ml diluted 1:1000 Siemens Healthcare Diagnostics). The membrane with antibody conjugate was incubated at room temperature for 3 hours or at 4° C. overnight with gentle agitation. The antibody was then discarded and the gel was washed three times with TTBS for 5 minutes each. The membrane was incubated with the alkaline phosphate or horse radish peroxidase substrate and the color developed and recorded. In some cases the membrane was imaged by exposure to X-ray film (Fisher) at a desired time (3 seconds to 10 minutes) and then developed using Kodak® GBX developer/fixer.

The results of the western blots obtained on human plasma with monoclonal antibodies to CTF are shown in FIG. 3. Results are typical for all monoclonal antibodies to CTF R1 and R2. FIG. 3a shows the results for the plasma of three non-diabetic (N) patients, three insulin resistant (IR) patients and three diabetic (D) patients. All show CTF was present in immunoglobulin at 160 kDa, immunoglobulin heavy chain at 55 kDa and immunoglobulin light chain at 26 kDa and fragments thereof. As samples were treated with mercaptoethanol, and mercaptoethanol breaks disulfide linkages, therefore the CTF was not attached to immunoglobulin by disulfide linkages. FIG. 3b shows the same patient samples after treatment with alkaline conditions (250 mM Tris buffer, pH 11.5, and 37° C. for 2 hrs). The treatments break CTF linkage to human immunoglobulin and CTF was detected. In FIG. 3c, the gel for alkaline treated samples was measured with anti-Human IgG-ALP, and the results demonstrated the human immunoglobulin was still present after the release of CTF. These alkaline conditions, and others that have been shown to break the ester bond between C3b and immunoglobulin chains, also liberated CTF from immunoglobulin (Lutz H. U. and Stammler P. Preferential formation of C3b-IgG Complexes in vitro and in vivo from nascent C3b and naturally occurring anti-band 3 antibodies J Bio Chem 268, 17418-426, 1993).

The results of the western blots obtained on liver, pancreas, muscle and mesenteric tissues of normal rats, diabetic rats and diabetic rats treated with AdipoR1 CTF25 (SEQ ID NO: 11) are shown in Table 3. Results are typical for all monoclonal antibodies to CTF AdipoR1 and AdipoR2 and treatments tested. All of the tissues show the presence of CTF immunoglobulins. The liver samples showed immunoglobulin light chain at 26 kDa and some full IgG and fragments at 100 and 160 kDa but no immunoglobulin heavy chain at 50 kDa. The pancreas samples showed heavy chain and some light chain but no full IgG. The muscle and fat samples showed heavy chain and light chains but no full IgG. Treatment with CTF did not increase bands as free CTF does not attach to immunoglobulin without activation of the peptides for forming covalent bonds. Differences in the amount of immunoglobulin chains with CTF were observed between individual rat and between normal and diabetic rats. All tissues contained IDE and TACE.

TABLE 3

CTF immunoglobulin in tissues

| | Primarily observed immunoglobulin chains with CTF | | |
|---|---|---|---|
| Tissue type | Normal rats | Diabetic rats | Treated diabetic rats |
| liver | Light chains | Light chains | Light chains |
| pancreas | Heavy chain | Heavy chain | Heavy chain |
| muscle | Heavy & light chains | Heavy & light chains | Heavy & light chains |
| mesenteric tissues | Heavy & light chains | Heavy & light chains | Heavy & light chains |

Further, target organ studies were performed. Two groups of rabbits (anti polyclonal CTF producers and non-producers) were harvested for liver, muscle, adipose, brain and pancreas for cryo slice slides. The tissues were stained for free CTF (mAb 461-4H11), CTF-IgG (mAb 444-1D12), tumor necrosis factor-α converting enzyme (TACE aka ADAM-17), insulin degrading enzyme (IDE) and IgG. Binding was conducted with a Fc receptor blocking peptide and using fluorescent labeled antibodies with a scanning microscope. The results showed the liver is the primary target organ for CTF absorption. Diseased liver, brain and pancreas exhibit increased absorption. Liver, brain and pancreas are where IDE resides (CTF acts on IDE). Muscle and some brown fat had TACE for releasing CTF. An immune response to CTF greatly increases absorption of CTF-IgG into the brain, pancreas and liver. The results are shown in Table 4. The brain and pancreas were sometimes weakly positive for CTF inside some tissue areas especially around the endothelial and interstitial areas showing lesions or white blood cells infiltration (WBC). Muscle was only positive on the outside membrane of the cell due to intact receptor. White adipose did not show CTF but there was some trace CTF build up in brown adipose.

TABLE 4

| | Liver | Cerebellum | Cerebral Rgt & left | Pancreas | Fat (adipose) | Muscle |
|---|---|---|---|---|---|---|
| CTF | Pos. 5+ | Pos 1+ | Pos 1+ | Pos 1+ | Neg. | Pos 1+ |
| TACE (CTF forming protease) | Neg. | Neg. | Neg. | Neg. | Pos | Pos |
| IDE (Protease inhibited by CTF) | Pos | Pos | Pos | Pos | Neg. | Neg. |
| IgG counter staining | Pos where CTF found | Pos where CTF found | Pos where CTF found | Neg | Neg | Neg |

Antibodies to CTF illustrated a greatly increased absorption of CTF-IgG and CTF into brain, pancreas and liver. This was in rabbits with anti-CTF antibodies. The rabbits had been inoculated with AdipoR1CTF 33mer (SEQ ID NO:1) attached to BSA and LBH. The results are shown in Table 5 and in FIG. 4.

TABLE 5

| Rabbits ability to produce polyclonal antibodies | CTF in Liver | CTF in Brain | CTF in Pancreas |
| --- | --- | --- | --- |
| Negatives | Pos 5+ | Pos 1+ | Pos 1+ |
| N = 3 | Pos 6+ | Neg. | Pos 1+ |
| Did not produce Anti CTF | Pos 5+ | Neg. | Pos 1+ |
| Positives | Strongly Pos. | Pos | Pos |
| N = 3 | | Pos 10+ | Pos 8+ |
| Anti CTF | Pos 35+ | Pos 11+ | Pos 12+ |
| producer | Pos 40+ | Pos 8+ | Pos 8+ |
| | Pos 30+ | | |

Further, target organ studies were performed. Three groups of rats were sacrificed and harvested for liver, muscle, adipose, brain, lymphnodes and pancreas for cryo slice slides. These three groups represented rats without diabetes, 2-4 weeks into early diabetes and late diabetes. All were characterized for diabetic status by oral glucose tolerance test (OGTT) and hbA1c test. The tissues were stained for free CTF (mAb 461-4h11), IgG-CTF (mAb 444-1D12), TACE, IDE and IgG. Biding was conducted in the presence of a Fc receptor blocking peptide and using fluorescent labeled antibodies with a scanning microscope. The results showed the lymph nodes are another primary target for CTF absorption. As diabetes progressed, the amount of CTF observed in the liver and lymph nodes increased. The brain and pancreas also exhibited increased absorption. These results are summarized in Table 6.

TABLE 6

| CTF | Normal Rats N = 3 | Short Term Diabetic Rats N = 3 | Long Term Diabetic Rats N = 3 |
| --- | --- | --- | --- |
| Liver | Neg. | Pos. | Pos. |
| | Pos. 2+ | Pos. 5+ | Pos. 6+ |
| | Neg. | Pos. 4+ | Pos. 7+ |
| | Neg. | Pos. 3+ | Pos. 5+ |
| Lymph Node | Neg. | Pos. | Pos. |
| | Pos. 5+ | Pos. 10+ | Pos. 5+ |
| | Neg. | Pos. 11+ | Pos. 11+ |
| | Neg. | Pos. 8+ | Pos. 5+ |

Cell culture mouse myocytes (C2C12) and green monkey epithelial cell (VERO) (American Type Cell Culture, ATCC, Manassa Va.) were maintained in culture using RPMI-1640 media, while normal cells were maintained with modified Eagle's medium (MEM). Both media contained 2 mM glutamine, penicillin (50 units/ml), streptomycin (50 μg/ml), and 10% fetal bovine serum. The media was cytokine free. Cells were grown at 37° C. in an atmosphere of 95% air and 5% $CO_2$ and propagated by splitting with 1 to 4 dilutions using PBS/EDTA at cell growth confluence. Cell lines were synchronized and induced with R1 CTF25 SEQ ID NO:11 or globular adiponectin. The results are shown in Table 7.

TABLE 7

CTF immunoglobulin in cells

Primarily observed immunoglobulin chains with CTF

| Cell type | Untreated | Treated with CTF | Treated with adiponectin |
| --- | --- | --- | --- |
| Myocyte | Heavy chains & full IgG | Heavy chains & full IgG | Heavy chains & full IgG |
| Epithelial cells | Heavy chains & full IgG | Heavy chains & full IgG | Heavy chains & full IgG |

Both cell lines expressed Adiponectin receptor 1 and lysates from both cell lines contained CTF immunoglobulin, comprising the heavy chain and full IgG but without the light chain form on denatured Western blots. As these are cell cultures grown in fetal bovine serum containing bovine IgG, the cells attach CTF to IgG. Therefore any cell expressing adiponectin receptors act as antigen presenting cells and cause activation of CTF for attachment to immunoglobulin (FIG. 2). See Golz for a list of cells and tissues expressing Adiponectin receptor 1 and 2.

The treatment of cell cultures with CTF R1 CTF25 SEQ ID NO: 11 did not increase CTF immunoglobulin as this CTF form does not to immunoglobulin without activation. Additionally, adiponectin treatment did not increase CTF immunoglobulin bands presumably, since the serum already contained adiponectin to bind to the receptor.

Blood fractions were also studied to see if CTF-IgG is in blood and if immune cells carry CTF. Cells were isolated by filtration and stained with antibodies for free CTF-IgG (mAb 444-1D12) and IgG with a fluorescent label. The cells were then counter stained with DAPI and anti-white blood cell antibodies (CD45, CD3 and CD19) with a second fluorescent label. Binding was conducted in the presence of an Fc receptor blocking peptide. The results were determined on a scanning microscope. The results showed that IgG CTF is carried on white blood cells (polymorphonuclear B and T cells). These polymorphonuclear B and T cells appear to be neutrophils and basophils. Red blood cells do not carry CTF. CTF and CTF IgG are detected by immunohistochemistry (IHC) separately from the full receptor. These results are shown in Table 8.

TABLE 8

| | RBC | WBC (CD45+) Polymorpho nuclear | T Cell CD 3 | B Cell CD 19 |
| --- | --- | --- | --- | --- |
| CTF Present on cell | Neg | Pos on many cell even with IgG blocking | Pos Cells observed in 10 mL blood | Pos Cells observed in 10 mL blood |
| IgG binding | Pos | Pos | Pos | Pos |
| Source | Human whole blood | Human whole blood | Human whole blood | Human whole blood |

It was confirmed that the receptor expression was not being detected, only IgG-CTF and CTF.

Example 2

Alkaline Conditions Liberate CTF from Ig; Correlation to Insulin Resistance

Plasma samples were treated with alkaline to free CTF from immunoglobulin to allow total plasma CTF to be measured. Plasma samples were collected from patients with glucose tolerance tests and diagnosis of diabetes (See Table 9). Samples were assayed by immunoassay based on two antibodies for CTF and a correlation of liberated CTF with insulin resistance was determined.

TABLE 9

Insulin resistant patient cohort

| Collection | Controls | Insulin Resistant | Diabetics |
|---|---|---|---|
| Glucose tolerance test correlation of plasma sample | N = 50 Negative oral glucose tolerance test (OGTT) & non diabetic with hbA1C <6.5%.. | N = 50 Positive OGTT & non diabetic with hbA1C <6.5%. | N = 50 Positive OGTT & diabetic with hbA1C >=6.5%. |

The typical sample ELISA plate was prepared by coating a plate first with an anti CTF antibody such as Mab 444-1D12 at a concentration of 12 µg/ml in tris buffered saline (TBS). The plate was then washed with TBS using an automated plate washer (5 times at 300 µL). The plate was then blocked with 1% bovine serum albumin in TBS. The plate was washed again with TBS. The CTF calibrators were prepared in TBS at pH 6.5 at 10, 5, 2.5, 1.25, 0.625, 0.312 and 0 ng/ml using CTFR125, the amino acid sequence of (SEQ ID NO: 11) HFYGVSNLQEFRYGLEGGCTDDTLL. Treated patient samples were prepared by mixing 50 µL of sample with 40 uL with Tris 50 mM at pH 10.5 for 1 h at 37° C. followed by pH neutralization with 120 uL of Tris 0.5 M at pH 5.2. The calibrators and samples were load at 100 µL. The plate was sealed and incubated with a shaker speed of 1000 rpm at 35° C. for 60 min per wells.

The typical assay ELISA plate was measured after washing again with TTBS to remove unbound CTF. A second anti CTF antibody conjugated to alkaline phosphatase (ALP) such as mAb 444-1D12 (Siemens Healthcare Diagnostic) at a concentration of 4.0 µg/ml in TTBS was applied at 100 µl to each well. The plate was sealed and incubated in a shaker at a speed of 1000 rpm at 35° C. for 60 min followed by washing with TTBS again. The amount of ALP in each well was measured using 1-Step™ PNPP substrate (Fisher Thermo Scientific) in a plate reader and incubated to 37° C. reading the plate on the hour using absorbance at 405 nm for 12 h.

TABLE 10

Insulin resistance correlation to free CTF

| R1 Total | Aver | sd | Min | Max |
|---|---|---|---|---|
| Normals | 671.3 | 1211.3 | 5.0 | 6951.3 |
| Diabetics | 1030.2 | 1662.0 | 19.6 | 7758.9 |
| Insulin res | 1241.5 | 2079.3 | 38.0 | 11137.0 |

The result of the correlation obtained is shown in Table 10. All patients were measure-able with low background and within a plate range of <10% CV and an assay range of 100 to 10,000 pg/mL. The total bound values increased 1.8 fold in patients with insulin resistance.

The instability of free CTF (SEQ ID NOs: 1 to 44) above pH 7.0 was confirmed. As a result, pH treatment had to be carefully controlled to obtain reproducible measurements of free CTF. Even with such controls, the between plate values variation was often ~20% and higher than desired for clinical applications. Free CTF is more stable below pH 7, preferably pH 6.5, as it typically resides in the acid environment inside the cell. Here as previously disclosed the free CTF form dimers. As immunoglobulin CTF is stable in pH less <8 and is the principle form of CTF found outside the cell, the measurement of immunoglobulin CTF was desired for clinical application.

Example 3

Identification of Immunoglobulin Chains Containing CTF

Commercial grade human serum proteins were western blotted with mAb444-1D12 ALP in accordance with the method of Example 1. The commercial grades tested included IgG (14506 Sigma Aldrich Chemical Co, St Louis Mo.), kappa light chain (AG744 Millipore Billerica, Mass. formerly Chemicon), lambda (P164-1 ScipacLtd, Kent UK), Fc fragment (AG744 Chemicon), IgA (1-0633 Sigma) and IgM (1-8260, Sigma) Immunoglobulin IgG is comprised of kappa and lambda light chains of approximately 26 kDa and two gamma heavy chains. IgA, IgM, IgD and IgE do not contain gamma heavy chain and instead are based on alpha, mu, delta, and epsilon heavy chains, respectively. All immuglobulin, IgG, IgA, IgM, IgD and IgE, do contain Kappa light chain. The results are summarized in Table 11.

TABLE 11

Immunoglobulin chains containing CTF

| Commercial grade human serum proteins | Observed band with western blot to R1 CTF monoclonal antibody | |
|---|---|---|
| | Gamma chain bands | Kappa chain bands |
| IgG | 50 kDa | 26 kDa |
| IgM | No bands | 26 kDa |
| IgA | No bands | 26 kDa |
| Kappa | No bands | 26, 15, 13 & 12 kDa |
| Lambda | No bands | No bands |
| Fc | No bands | No bands |

The data showed that CTF is attached to gamma and kappa chains of IgG. No free CTF as monomer or dimer was observed in IgG. The data also showed that CTF is attached to the kappa chains of IgA and IgM. Kappa chain fragments smaller than 25 kDa were observed. IgD and IgE also contain kappa chains and therefore are also expected to contain attached CTF. The Fc region of the gamma heavy chain, also known as the effector function domain, did not contain CTF bound to the heavy chain fragments of 50 or 25 kDa. This indicates that CTF is attached to gamma and kappa chains in the Fab region of IgG.

As CTF is integrated into IgG, IgA, IgM, IgD and IgE isotypes in the kappa chain, using an anti kappa and anti CTF monoclonal sandwich assay measures CTF bound in all immunoglobulins. In contrast, an assay employing an anti gamma and anti CTF monoclonal sandwich assay measures CTF bound only in the IgG isotype. Similarly, other antibodies specific for IgG, IgA, IgM, IgD or IgE allow monoclonal sandwich assay that measure CTF bound in that form.

Example 4

Correlation of Immunoglobulin CTF

Plasma samples were measured for CTF immunoglobulin using an ELISA method with monoclonal antibody for CTF R1 and CTF R2 and an antibody for immunoglobulin using a monoclonal antibody for kappa or gamma immunoglobulin chain conjugated to ALP. The ELISA methodology used was the same as previously described without the alkaline treatment of the samples, and assigning patient samples with CTF immunoglobulin as standards and using shorter read times for the assay.

The bound CTF immunoglobulin assay was used to test the insulin resistant patient cohort (See Table 12). All patients were measureable with low background, and within plate range of <10% CV and an assay range of 100 to 10,000 pg/mL. Extremely elevated free CTF was still detected but more so in the normal samples. Additionally the between-plate CV was reduced to <10% and the standard deviation within the patient group was reduced.

TABLE 12

Insulin resistant correlation to CTF Immunoglobulin

|  | Aver | sd | Min | Max |
|---|---|---|---|---|
| CTF R1 Gamma | | | | |
| Normals | 1114.3 | 1431.6 | 218.2 | 7476.1 |
| Diabetics | 814.0 | 594.1 | 202.2 | 2630.9 |
| Insulin res | 558.5 | 384.7 | 147.2 | 2263.1 |
| CTF R1 Kappa | | | | |
| Normals | 1011.0 | 1303.7 | 78.9 | 6422.3 |
| Diabetics | 897.4 | 718.0 | 289.2 | 4465.4 |
| Insulin res | 645.3 | 302.2 | 269.6 | 1480.4 |
| CTF R2 Gamma | | | | |
| Normals | 2118.2 | 1581.2 | 415.7 | 9394.9 |
| Diabetics | 1674.9 | 829.1 | 222.9 | 4099.6 |
| Insulin res | 1412.5 | 704.0 | 441.6 | 4218.2 |
| CTF R2 Kappa | | | | |
| Normals | 1205.1 | 772.7 | 320.4 | 4598.6 |
| Diabetics | 1043.1 | 428.6 | 246.6 | 2026.0 |
| Insulin res | 981.4 | 458.1 | 202.8 | 2292.8 |

The results of the correlation are shown in Table 12. A 2.0 fold decrease in CTF immunoglobulin in plasma was observed in patients with insulin resistance. The CTF immunoglobulin accumulates in tissues and cells causing insulin resistance. Measurements were similar when measuring CTF R1 immunoglobulin versus CTF R2 immunoglobulin. Measurements were similar when measuring kappa chain immunoglobulin versus gamma chain immunoglobulin. Of the combination CTF R1 gamma chain immunoglobulin had the largest decrease in insulin resistance. Here, using a threshold of <300 pg/mL of CTF immunoglobulin as an indication of insulin resistance the diagnostic sensitivity was 70% and specificity was 70%.

These results were confirmed using the protocols of Example 13. A study was designed to compare non-diabetics to early diabetics and late diabetics. The IgG-CTF assay was used with whole blood samples obtained from patients who underwent fasting glucose screening. Patients were defined as normal if they had both a normal fasting whole blood glucose of <100 mg/dL and normal whole blood HbA1c of <6.5%. Patients with an abnormal whole blood fasting glucose (>135 mg/dL) underwent an oral glucose tolerance test (OGTT) Patients with an abnormal OGTT result (plasma glucose values of >126 mg/dL at 0 hour or >200 mg/dL at 2 hour) or an abnormal whole blood HbA1c of <6.5% were classified as pre-diabetic or of impaired glucose tolerance.

Through this process 101 patients were classified as non-diabetic and 127 patients were classified as diabetic. IgG-CTF by ELISA assays were performed on all diabetic and non diabetic patients The IgG-CTF results are summarized in Table 13 and 14.

TABLE 13

|  | IgG-CTF Normal | IgG-CTF Abnormal |
|---|---|---|
| Not Insulin Resistant | 85 subjects | 16 subjects |
| Insulin Resistant | 22 subjects | 105 subjects |

Positives were defined as impaired glucose tolerance with a 120 min value of greater than 140 mg/dL or long term diabetic. The threshold used was 5.5 ng mL of IgG-CTF. The sensitivity was 83.2%. The specificity was 84% the positive predictive value (PPV) was 87% and the negative predictive value (NPV) was 80%. PPV was calculated as true positives (TP)/(TP+false positives (FP)). NPV was calculated as true negatives (TN)/(TN+false negatives (FN)).

TABLE 14

|  | IgG-CTF Normal | IgG-CTF Abnormal |
|---|---|---|
| Not Insulin Resistant | 90 subjects | 19 subjects |
| Insulin Resistant | 17 subjects | 102 subjects |

The threshold used was 5.5 ng/mL of IgG-CTF and the PPV was 84% and the NPV was 84%.

The conclusions drawn from these experiments is that a good correlation was achieved. 0 and 120 minutes gave the same IgG-CTF values, so it is a chronic marker that only requires a 0 time measurement.

In addition testing for CTF immunoglobulin was conducted in a cohort of serum samples from patients with abnormal cell growth (See Table 15). Patients with metastatic and localized carcinomas were separated from nonalcoholic steatohepatitis (NASH) which is characterized by insulin resistance and alcoholic hepatitis and autoimmune hepatitis which is characterized by the presence of inflammatory cells in the liver.

TABLE 15

Cancer and liver disease patient cohort

| Collection | Normals N = 30 | Breast cancer N = 9 | Pancreas cancer N = 5 | Liver disease N = 23 |
|---|---|---|---|---|
| Abnormal cell growth population (Serum) | No History of Cancer, Liver Disease, Diabetes or Metabolic Syndrome | Comprised of N = 8 localized carcinomas and N = 1 metastatic cancer | Comprised of N = 4 localized carcinomas and N = 1 metastatic cancer | Comprised of N = 12 Nonalcoholic steatohepatitis (NASH); N = 3 Alcoholic hepatitis; N = 6 Autoimmune |

TABLE 15-continued

Cancer and liver disease patient cohort

| Collection | Normals N = 30 | Breast cancer N = 9 | Pancreas cancer N = 5 | Liver disease N = 23 |
|---|---|---|---|---|
| | | | | hepatitis; N = 2 Hepatocellular carcinoma. |

The results of the correlation are shown in Table 16. A 2.5 fold increase in the CTF immunoglobulin was observed in patients with breast and liver cancer. A 1.7 fold increase was observed in patients with metastatic cancer. Patients with pancreatic cancer had decreases in CTF immunoglobulin. Patients with proliferative liver diseases such as nonalcoholic steatohepatitis (NASH), alcoholic hepatitis and autoimmune hepatitis had even more significant increases in CTF immunoglobulin, up to 5.5 fold increase. While not being bound to a particular mechanism of action, it is believed the insulin producing pancreas is protected from being CTF immunoglobulin while the insulin degrading liver is more susceptible to CTF immunoglobulin.

TABLE 16

Cancer and liver disease patient cohort

| | AdipoR1 kappa pg/mL | sd | Change in CTF |
|---|---|---|---|
| Normal | 594.9 | 724.9 | 1 |
| Breast cancer | 1486.1 | 1692.9 | 2.5 |
| Metastatic cancer | 1028.8 | 11.8 | 1.7 |
| Pancreatic cancer | 327.5 | 194.9 | 0.6 |
| Hepatocellular carcinoma | 1512.3 | 483.6 | 2.5 |
| Autoimmune Hepatitis | 2028.7 | 1145.6 | 3.4 |
| Nonalcoholic Steatohepatitis (NASH) | 2457.3 | 1570.4 | 4.1 |
| Alcoholic Hepatitis | 3279.2 | 2569.0 | 5.5 |

Example 5

Isolation of Native CTF Immunoglobulin

Native CTF immunoglobulin was isolated by the western blot method. Alternatively, native CTF immunoglobulin was isolated by capturing it onto polymer resin beads conjugated with monoclonal antibody mAb 444-1D12. The PolyLink Protein Coupling Kit (Bangs Laboratories Inc.) was used for this conjugation. Other capture beads and particles commonly used worked as well. Native CTF immunoglobulin was released from capture bead by pH adjustment. It could also be purified by fractionation into IgG by protein A column purification. Purity and identification could be established by western blot to anti human kappa chain, anti human gamma chain and anti CTF antibodies. Mass spectrometry was also used for peak identification. The major forms immunoglobulin identified to include IgM, IgG, Fab2, Ig, gamma chain and light chain. The results are shown in Table 17.

TABLE 17

| | Observed kDa in Western blotts | | | | | |
|---|---|---|---|---|---|---|
| Band Id | Plasma | Fat Tissue | Liver Tissue | Muscle Tissue | Pancreas Tissue | Myocyte Cell Culture |
| IgM | 250 | | | 200 | | 200 |
| IgG | 160 | | | | | |
| Fab2 | 100 | | 100 | 110 | | 100-110 |
| unk | | | 70 | 80 | | 60 |
| gamma heavy | 55 | | | 55 | 50 | |
| AdipoR1 | | 37-45 | 43 | 37-45 | | 47 |
| Light chain CTF | 25 | 25 | 25 | 25 | 25 | |
| Light chain CTF Dimer | 22 | 22 | 22 | 22 | 22 | |
| | 8 | | | | | |

Table 17 shows the mass for AdipoR1 receptor is 43 kda for the full length form. The full receptor has shown up in tissue samples containing membranes and not plasma. The tissues did not generally contain detectable dimer, but this could be below the detection limit of the westerns.

Analysis by ELISA comparing IgG-CTF to IgG showed the percentage of IgG CTF in patient plasma was found to be <0.2% of all plasma IgG in most patients. This percentage was similar for IgG CTF R1 and R2. The percentage of IgM CTF was typically lower, but in patient plasma was found to be approximately <0.03% of all plasma IgM in most patients. This percentage was similar for R1 and R2 attachment. The ratio of CTF to IgG was typically 1 to 2 in most patients with a range of 1 to 5.

ELISA studies with IgM, IgG, gamma, Kappa and Fab antibody cross reactivity were tested in plasma for CTF bound fragments and did confirm IgM, IgG, gamma, Kappa and Fab were present. Additionally it was confirmed that two CTFs are typically on an IgG.

Example 6

Isolation of Antigens to Native CTF Immunoglobulin

Cells binding native CTF Immunoglobulin can be isolated from biological materials, such as tissues, fluids and cell cultures using the CTF-IgG assays (IHC or ELISA) disclosed herein. Isolation methods of the cells often use antibodies attached to magnetic particles, fluorescent particles, capture beads and other materials useful for isolating and sorting cells such as in flow cytology, microscopic imaging, filtration and other. The native CTF Immunoglobulin can serve as antibodies in the capture phase or for sorting by cell detecting.

The native CTF Immunoglobulin was attached to fluorescein isothiocyanate (FITC) as a signal generating compound. Cancer cells were isolated by a filtration method, to isolate circulating tumor cells from other cells in the blood. Patient blood was lysed by ammonium chloride to remove red blood cells but not white blood cells or cancer cells. White blood cells or cancer cell were captured on a 8 μm pore membrane which allows the red blood cells to pass. The membranes are imaged with a scanning fluorescent microscope to find the cancer cells and white blood cells binding to native CTF Immunoglobulin. White blood cells were counterstained with CD3, CD45 and CD19 antibodies with Cy5 dye to confirm the identity of CTF immunoglobulin binding cells as neutrophils, beta cells and T cells. Cancer cells were counterstained with EpCAM antibodies with Texas Red dye to confirm the identity of CTF immunoglobulin binding cells as carcinoma cells.

The individual cells that bind to native CTF Immunoglobulin and are removed from the membrane and may be amplified by cell culturing. This cell isolation and amplification may be useful for cell response to identify biochemical ways to prevent CTF from connecting to IgG, to block CTF-IgG from absorbing into tissue and to alter the impact of CTF-IgG on immune cells. Thus, this measurement can be used to identify potential drugs. These cells can also be used for the isolation of molecules that bind to CTF-Immunoglobulin to identify potential new drugs.

For example, the antigen can be isolated from cell lysates by capturing them onto a polymer resin beads conjugate with native CTF Immunoglobulin as the capture phase. Affinity purified antigens are released from the beads.

Example 7

Isolation of Specific Immunoglobulins Binding to CTF Immunoglobulin and Antigens The CTF bound to immunoglobulin and other proteins can be used to make monoclonal antibodies. Also, the affinity purified antigens to native CTF Immunoglobulin can be used to make monoclonal antibodies (immunoglobulin).

Monoclonal antibodies to these antigens were made by fusing myeloma cells with the spleen cells from a mouse that has been immunized with the antigen on a standard carrier proteins such as keyhole limpet hemocyaninn (KLH), bovine serum albumin (BSA), ovalbumin (OA) or the likes. Antibody-producing cells are fused with cells that grow continuously in culture to form hybridomas in selective culture HAT medium. The selective culture medium is called HAT medium because it contains hypoxanthine, aminopterin, and thymidine. This medium is selective for fused (hybridoma) cells. Single hybridoma producing only one antibody to one antigen were isolation. The single hybridoma divides to produce a large population of 'clones' all making the same "monoclonal" antibody. Living hybridomas are frozen indefinitely in liquid nitrogen.

Example 8

Isolation of Specific Antigens to CTF Immunoglobulin

The monoclonal antibodies can be used to isolate specific antigens to CTF immunoglobulin by purification of cellular antigen by capturing onto a polymer resin beads conjugate with specific monoclonal antibodies from Example 6. The PolyLink Protein Coupling Kit (Bangs Laboratories Inc.) can be used for this conjugation. Other capture beads and particles commonly used can be employed as well. The antigen specifically binding the monoclonal antibody can be released from capture bead by pH adjustment. Purity and identify can be established first by western blot to native CTF immunoglobulin and monoclonal antibodies from Example 6. The reactive bands can be isolated and identity determined by peptide sequence of N termal tail or by mass spectroscopy.

Example 9

CTF Conjugation of Immunoglobulin

CTF Immunoglobulin was produced by attachment of CTF R1 CTF25 SEQ ID NO:11 to immunoglobulin Fitgerald product code 30-AI17) which attaches a peptide to the C-terminus of another peptide through succinimide esters (e.g. MBS, SMCC) which binds free amino groups and vystein residues. These materials were used as standards for the ELISA methods. This same CTF attachment process can be done with many other immunoglobulins. For example, those isolated from Example 6 or other immunoglobulin. For example, CTF could also be attached to trastuzumab, fulvestrant, tositunomab, ibritumomab, imatinib, lenalidomide, cetuximab, dasatinib, pantumumab, lapatinib, and nilotinib. In practice, maleimide-Activated IgG was treated with the sulfhydryl (—SH) moieties on cysteine residue of CTF to produce synthetic CTF-Immunoglobulin.

Example 10

CTF Immunoglobulin Impact of Insulin Response and Cell Growth

The CTF was previously found to impact insulin response in animal models. Insulin response was measured by glucose tolerance testing in animal models as previously disclosed (Int. Publ. No. WO 2007/120,311). Animal models treated with CTF were compared to an untreated group to determine the response and effectiveness. Similarly, animal models can be treated with CTF immunoglobulin isolated from native samples or produced as a synthetic CTF Immunoglobulin conjugate. Animal models can also be treated with antigens to CTF Immunoglobulin or specific immunoglobulins to said antigen.

Insulin resistance and abnormal cell growth can also be measured using cell models. In general the cell cultures, such as cancer cells (e.g., MCF, MDA SKBR), myocytes (C2C12) and green monkey epithelial cell (VERO) (American Type Cell Culture, ATCC, Manassa Va.), are maintained in culture using RPMI-1640 media, while myocyte and cancer cells are maintained with modified Eagle's medium (MEM). Both media contained 2 mM glutamine, penicillin (50 units/ml), streptomycin (50 μg/ml), and 10% fetal bovine serum containing insulin and adiponectin. Cells were grown at 37° C. in an atmosphere of 95% air and 5% $CO_2$ and propagated by splitting with 1 to 4 dilutions using PBS/EDTA at cell growth confluence. Cell lines can be synchronized and can be induced (treated) with native CTF immunoglobulin; plasma with CTF-IgG, synthetic CTF immunoglobulin conjugate, or with antigens to CTF Immunoglobulin or immunoglobulins to said antigens.

Insulin response in treated cell culture can be measured directly by binding insulin to the insulin receptors or by measuring loss of intercellular insulin. Less insulin binding indicates a lower insulin receptor level and insulin response. Binding to the receptor is measured by binding whole cells to ELISA plate with incubation for 12 h, wahing the plate was with TBS, blocking with 200 uL of Blocker Casein in PBS (Thermo Fisher 37528) followed by washing with TTBS. Each well was incubated with insulin-Biotin (5 ng/mL or 1.4 uM) in 25 mM Tris, 25 mM HEPES, 0.1M NaCl, and 10%

Trehalose adjusted to pH 7.5. After 1 h of incubation at 37° C., the plate was washed with TTBS, incubated for another hour with streptavidin-ALP (0.3 mg/mL or 0.074 μM), and washed. Bound ALP was measured by adding para-nitrophenol phosphate.

Insulin resistance or abnormal cell growth in treated cell culture can be measured using cellular signals caused by insulin. Insulin activates glucose transport, glycogen synthesis, protein synthesis, cell proliferation, cell migration adhesion, survival, protein synthesis, nitroxoide synthesis and neuroprotection, through the PI3 Kinase/Akt and MAPK/ERk signaling and the resulting tubulin polymerization, beta cartenin degradation, cyclin D1 degradation, and mTor signaling. In general, insulin controls the body's cell proliferation and accelerates the entrance of glucose into the liver and muscles, with insulin secretion determined by the level of blood sugar. In contrast, adiponectin signals, like leptin and alpha-adrenergic receptor, increases glucose uptake, glycolysis, fatty acid oxidation, blood pressure and flow; and decreases glycogen synthesis, gluconeogenesis, fatty acid synthesis, sterol synthesis, lipolysis, cell proliferation through the AMPK synthesis, in general, burning the body's energy and stopping long energy storage.

Kinase phosphorylation assays can be generally conducted by adding cells to the microtiter plate wells and fixing them with 100 uL of 4% formaldehyde in PBS. The plates were kept for an additional 20 min at room temp and then covered with parafilm and stored at 4° C. until assayed. ELISA measurements of the relative increase in phosphorylation of Akt and PIK3 were performed according to the ELISA manufacturer's instruction (Superarray, Frederick, Md.). Measurements of the relative increase in MAPK ERK phosphorylation were performed according to the ELISA manufacturer's instruction (Assay Designs, Ann Arbor Mich.). Results were repeated in 3 independent experiments with new cultures. Cells were fixed to the microtiter plate followed by removal of the fixing buffer and cell quenching performed with $H_2O_2$ and $NaN_3$. The quenching buffer was removed and the plate was heated, washed, and blocked. This was followed by 1 hour incubation with primary antibodies for Akt, Phos-Akt, $PI_3K$, and Phos-$PI_3K$ (1:100 dilution). Each antibody and induction condition was tested in separate triplicate wells. The unbound primary antibodies were removed by washing and the plate was then incubated for 1 h with a secondary antibody conjugated to HRP (1:16 dilution). The plate was washed twice and developing solution was added. After incubation, the resultant dark blue color formed after the addition of stop solution was read at 450 nm.

Insulin resistance or abnormal cell growth can also be measured by cell apoptosis signaling. Signally of apoptosis is inhibited by nuclear factor kappa-light-chain-enhancer of activated B cells (NF-kappaB) which is controlled by tumor necrosis factor (TNF alpha). Signaling of apoptosis is inhibited by PI3 kinase/Akt kinase phosphorylation, which is controlled by insulin. Therefore CTF induced insulin resistance and CTF inhibition inhibited TNF alpha release, both favoring apoptosis signaling.

Apoptosis signaling is a regulated cellular suicide mechanism characterized by nuclear condensation, cell shrinkage, membrane blebbing and DNA fragmentation. Activation of apoptosis can be measured by activation of caspase proteases, namely caspase 3, 5, 6, & 9. These caspases are the central regulators of apoptosis, and are a definitive measure of executed apoptosis. Apoptosis signaling can also be measured by phospatidylserine analysis using fluorescent sensors, a measure of membrane changes during apoptosis process (B. D. Smith, Cell Death and Differentation 2003; 10; 1357-9).

Apoptosis assays by caspase activation are generally conducted by using various cell extracts and supernatants. Western blots were performed against anti-caspase antibodies (3/8/9) (Cell Signaling Technology, Inc. Danvers, Mass.). The electrophoresis was run under standard conditions using Tris-Glycine-SDS buffer at 18-20 mAmp with 3 μg BioRad prestained standards. After electrophoresis the proteins were transferred from the gel onto a nitrocellulose membrane at 80 V for 1 hour or 40 V overnight at 4° C. The transferred proteins were reacted with the specific antibodies (1 mg/mL) mentioned above after 1 hour blocking with casein blocker. After washing off the unbound antibody and blocking with TBS containing Tween®-20, the blotted membranes were incubated with ALP-conjugated corresponding second antibody for another hour. Finally, the cross-reactivity of the samples to the antibodies was monitored by addition of 66 μl of nitro blue tetrazolium (50 mg/ml 70% DMF) and 35 μl of bromo chloro indolyl phosphate (50 mg/ml DMF, 100%) in 10 ml, TBS.

Apoptosis assays using phosphatidyl serine analysis are generally conducted by using viable cells. Induced cells were treated with PSS-380 dye to recognize phosphatidyl serine on the outer leaflet of the apoptotic cells (9). Cells were plated onto Falcon Microslide System (Fisher) and washed 2 times with TES buffer (5 mM N-tris [Hydroxymethyl]-2-aminoethane-sulfonic acid: TES, 150 mM NaCl, pH7.4), which was followed by incubation with 200 μL new TES buffer containing 25 μM PSS-380 at 37° C. for 10 minutes. The buffer was removed after staining, and the cells were washed with TES buffer once before observation for fluorescence. Phase contrast images were used to locate regions of fluorescent signals and to calculate the percentage of affected cells.

The expected result of cancer cell culture induced with native CTF immunoglobulin; synthetic CTF immunoglobulin, antigens to CTF Immunoglobulin and specific immunoglobulin to said antigen are shown below in Table 18.

TABLE 18

Impact on insulin response and cell growth

| | Insulin response | Cell growth. |
|---|---|---|
| Normal | Base line | Base line |
| Native CTF immunoglobulin | Decrease | Decrease |
| Synthethic CTF immunoglobulin | Decrease | Decrease |

Example 11

Impact of Immunoglobulin CTF on Measurement of CTF

Plasma samples were measured by three assays for CTF. These three assays are compared in Table 16. The first assay was a sandwich assay for free CTF using an ELISA method with a monoclonal antibody for CTF and a polyclonal antibody for CTF conjugated to ALP.

The second assay was a sandwich assay for free CTF non covalently bound to albumin using an ELISA method with a monoclonal antibody for CTF and a polyclonal antibody for human albumin conjugated to ALP. The free CTF molecule was found to associate and bind strongly in a "non-covalent" fashion to albumin. As a result, almost all free CTF in plasma is associated with albumin. Albumin binding was confirmed by treating plasma with CTF bound to a capture bead. The proteins bound to the CTF were dissociated (broken) on western blot with SDS denaturing gel electrophoresis and the last few N-terminals peptides sequenced to identify the binding protein as albumin. This bond was not broken in a free CTF immunoassay.

The third assay was a sandwich assay for CTF bound covalently to immunoglobulin chains using an ELISA method with a monoclonal antibody for CTF and a monoclonal or polyclonal antibody for human immunoglobulin chains conjugated to ALP. The CTF molecule was found to be covalently attached "and not just associated." As a result, almost all CTF attached to immunoglobulin in plasma cannot be dissociated (broken) on western blot with or without denaturing or in an immunoassay. Where albumin associated with CTF can be dissociated (broken) on western blot with denaturing or in an immunoassay washing procedure. Washing allows removing this interference association of albumin. The amount of IgG CTF in human blood is in far excess to the amount of free CTF or albumin associated free CTF. Therefore, both the impact of free CTF and albumin are reduced and not interferences to the IgG CTF assay.

A comparison of clinical performance of these assays is shown below in Table 16. The three immunoassays were used to test 100 plasma samples from patients and the results were compared to standards. The free CTF and CTF albumin assays used synthetic CTF peptide as a standard and for calibration and the CTF immunoglobulin assay synthetic CTF peptide conjugated to human IgG. The ideal immunoassay for clinical sample testing would maintain a high correlation (R2>0.95) to the standard and not suffer an increase in the background (<10% increase at detection limits caused by interference in the clinical sample).

TABLE 20

| SEQ ID NO: | AdipoR | Antibody Clone | Amino Acid Sequence |
|---|---|---|---|
| 49 | 1 | 461-4H11 | HVLVVAAAFVHFCYS |
| 50 | 1 | 444-1D12 | HFYGVSNLQEFRYGLEGGCTDDSLL |
| 51 | 1 | 515-4D6 | GGCTDDTLL |
| 52 | 2 | 510-6B6 | GGCSEEDAL |

After one month, ocular bleeds were taken from each mouse and titered by ELISA against the immunogen to assess the immune response. The mice showing the best response were boosted by injection of 100 μg/mouse with the immunogen. After four days, mice were sacrificed and their spleens used for fusion according to the method of Kohler and Milstein, Nature 256:495 (1975). The splenocytes were fused with SP2-0 Ag14 myeloma cells using PEG (polyethylene glycol) solution with a ratio of splenocytes to myeloma cells of 5:1 and plated into 96 well plates using 50% PEG/HAT growth media. After 7-10 days of incubation at 37 degrees Celsius, fusion cultures were monitored for growth by feeding every 3-4 days utilizing the HAT (hypoxanthine, aminopterin, thymidine) selection method followed by subculturing with HAT growth media.

After 2-3 weeks, the wells having hybridoma colony growth were tested by ELISA to determine which growths produced an antibody immune response to the peptide. The 96 well plate cultures were tested with the uristatin peptide at 100 μg/mL coated plates. After coating plates overnight at 2-8° C., all plates were washed and blocked. Cell culture supernatants were then applied 100 μl/well for one hour at room temperature. After washing plates, Goat anti-mouse IgG Horse Radish Peroxidase at 1:2000 dilution was applied at 100 μL/well for one hour. Plates were washed once again

TABLE 19

Method comparison

| Assay | Increase in background at detection limit (%) | Correlation Slope (R2) | Interference by CTF-IgG | Interference by CTF | Interference by Albumin |
|---|---|---|---|---|---|
| Free CTF assay | Up to 1762% | 0.90 | Yes | No | Yes |
| CTF-immunoglobulin assay | 8% | 0.98 | No | No | No |
| CTF-albumin assay | Up to 256% | 0.85 | Yes | Yes | No |
| Ideal | <10% | 0.95 | No | No | No |

The assay for CTF-immunoglobulin did not suffer interference and was suitable for clinical testing.

Example 12

Preparation of Monoclonal Antibodies

BALB/c mice were immunized with 100 μg/mouse of a synthetic AdipoR1 or AdipoR2 peptide immunogen composition. These AdipoR1 or AdipoR2 peptide immunogen compositions included as shown in Table 20:

followed by OPD (o-phenylene diamine dihydrochloride) substrate and read at 490 nm on a Spectra Max plate reader.

The colonies giving a positive response were transferred to 24 well plates for further expansion and retesting to verify the positive results. The colonies testing positive were further expanded in six well plates in Iscove's Modified Dulbecco's Medium (IMDM) with 10% Fetal Bovine Serum (FBS). After expansion, the colonies were frozen at −70° C. and then transferred to liquid nitrogen for long-term storage. Based on ELISA results using the purified peptide, various clones were further expanded in IMDM, 10% FBS and frozen down.

Antibody-producing cells made using the above protocol were deposited with the American Type Culture Collection ("ATCC") (10801 University Blvd., Manassas, Va. 20110-2209) on Feb. 21, 2012 and have been assigned Accession No. PTA-461-4H11.2A4 for cells producing mAb 461-4H11, Accession No. PTA-444-1D12.1H7 for cells producing mAb 444-1D12, Accession No. PTA-515-4D6.1B10 for clone 515-4D6, and Accession No. PTA-510-6B6.1G1 for cells producing 510-6B6.

Example 13

Bound Assay Protocol

These methods can be used to measure IgG-CTF in a correlation study to insulin resistance. The materials include the anti R1 CTF antibody Mab 444-1D12-1h7 at a. concentration of 2.5 mg/mL was diluted 150 uL of the antibody into 10 mL TBS for plate coating. Alternatively, anti R1 CTF antibody Mab 461-4H11.2A4 at a concentration of 1.25 mg/mL was diluted 300 uL of the antibody into 10 mL TBS for plate coating. Alternatively, anti R2 CTF antibody Mab 510-6B6-1G11 at a concentration of 0.47 mg/mL was diluted 1000 uL of the antibody into 10 mL TBS for plate coating. Anti human IgG antibody conjugated to ALP (anti IgG ALP) [Monoclonal Anti-Human Fab antibody produced in mouse by Siemens as product 7601MR was conjugated to Alkaline Phosphatase (ALP) (Biozyme ALPI12G lot 1662AA)], The anti IgG ALP was purified as 0.3 mg/mL stock which was diluted at 25 µL into 10 mL 0.05% T-TBS for use in the assay. The testing standard was made from human IgG (Fitzgerald product code 30-AI17) conjugated to the CTF R1 25mer (SEQ ID NO: 11) as described in Example 9. TBS without Tween® was made from BupH Tris Buffered Saline (Fisher Catalog # PI-28376) and is 25 mM tris and 0.15 M sodium chloride at pH 7.2. Blocking Buffer was Super blocker and it was used as supplied (Pierce), T-TBS was prepared by adding 10% Tween®-20 (Bio-Rad Catalog #141-0781) into TBS to make 0.05% Tween®-20, The calibrator buffer was PBE with 1% BSA (SigmaP3688) with 1.92 g/L citrate (0.1 M) pH adjusted to 6.4. For reading the immunoassay, a 96-well ELISA plate was used (Costar cat #3590) EIA plate with flat bottom and high binding Fisher Catalog #07-200-35, Corning™ cryogenic vials 1.2 mL C at 430658 were used for storage. BD Vacutainer® K2EDTA 10.8 mg sterile ref 367893 plastic tube and sodium heparin, glass tube ref 8091437 and gray top glucose tubes were also used.

The first step was to coat eight plates (Costar 96-Well EIA/RIA Plates Flat Well; High Binding) with a mAb for CTF at a concentration of 12 µg/ml in TBS. 100 µl/well coating solution was applied to the plate. The plate was sealed and allowed to incubate in the refrigerator (4° C.) overnight (~5 pm to ~9 am) or for 3 hours at room temperature. The coating solution was discarded by pipetting to drain off thoroughly. Plates to be stored were not washed and they were sealed with a plate sealer (Fisher Scientific Catalog #NC9479592) and put into a sealed bag with a desiccant. They were stored –20° C. until the day of use. The coated plates last three month.

The second step was blocking preparation of one plate for 40 patients. Each well was washed 5 times with 300 µl TBS, using an automated plate washer. Next 300 µl of Super Blocker was added to each well for blocking. The plate was incubated with a shaker speed of 1000 rpm (setting 5) at 37.5° C. for 60 minutes. The plate was washed 5 times with 300 µl 0.05% T-TBS, using an automated plate washer.

The third step was to prepare the sample calibrator by performing the following dilutions of concentrated synthetic CTF-reagent (20 µL IgG-CTF at 18.8 mg/µL in 10 ml PBS) to make a stock. This stock can be stored (e.g., refrigerated) for 3 months. Calibrators were made in calibrator buffer (PBS+Citrate+1% BSA at pH 6.4). Calibrators must be made fresh daily. The calibrators were made up according to Table 21.

TABLE 21

| Cal | Concentration | Dilution |
|---|---|---|
| 5 | 0.3 µg/ml | 300 µl Stock to 700 µl calibrator buffer |
| 4 | 0.15 µg/ml | 300 µl Cal 5 to 300 µl calibrator buffer |
| 3 | 0.06 µg/ml | 100 µl Cal 5 to 400 µl calibrator buffer |
| 2 | 0.02 µg/ml | 50 µl Cal 5 to 450 µl calibrator buffer |
| 1 | 0 µg/ml | calibrator buffer |

The fourth step was to prepare the samples of the patients. 50 µl of samples (43 per plate) was added into duplicate lane wells in the polypropylene sample plates. 600 µl TBS was added and mixed well (plate can be stored at this point at 4° C. for up to 5 days or –20° C. for at least 5 days. 50 µl of diluted sample (1:12) and 50 µL of calibrator were transferred into individual wells of blocked ELISA plates.

The fifth step was the immunoassay binding and washing for one plate at a time. The plate was sealed and incubated with a shaker speed of 1000 rpm at 35° C. for 60 minutes. The plate was washed 5 times with 0.05% T-TBS using an automated plate washer. 100 µl of Anti IgG alkaline phosphatase mAb was applied to each well in 0.05% T-TBS. The plates were sealed and incubated with a shaker speed of 1000 rpm at 35° C. for 60 minutes. The plates were washed 5 times with 0.05% T-TBS using an automated plate washer.

The sixth step was the immunoassay binding and washing for one plate at a time. PNPP substrate was prepared (Sigma Catalog #N189) fresh by dissolving 1 silver and 1 packet tablets into 10 ml of PNPP buffer at room temperature. Then, 90 µl of PNPP was added to each well. The plates were placed in the plate reader and incubated at 37° C. reading the plate on for 16 min using absorbance at 405 nm/950 nm every 2 minutes.

Example 14

Cancer and Blood Cell Staining and Tissue Sample Staining for Tissue Isolation The following are antibodies materials that can be used for tissue testing. They were used for tissues from rats and rabbits. Anti-CTFR1-FITC Mouse monoclonal mAb (clone 444-1D12 Ekhart Ind.) at 2.58 mg/mL (F to P 4:3) when diluted 10 uL in 10 mL PBS. Anti-CTFR1 Mouse monoclonal mAb (clone 461-4H11 Ekhart Ind.) was used with anti-mouse mAb FITC goat pAb of 1.0 mL at 2 mg/mL (clone UCHL1 PE ab6785 Abcam Inc.). Anti-TACE (ADAM17) mouse mAb (R&D systems MAB2129) was used with Anti-mouse FITC goat polyclonal antibody conjugated to FITC (Abcam ab6785). Anti-IDE (insulysin) goat pAb (R&D systems AF2496) was used with Anti goat FITC donkey polyclonal antibody conjugated to FITC (Abcam 97109).

The following are methods that can be used for cell isolation. Cellular material was filtered through a 8 µm pore membrane which allows the red blood cells to pass. The membranes were imaged with a scanning fluorescent microscope to find the cells binding to native CTF Immunoglobulin using: Anti-CD 45 TR (Ekhart Ind.) with Anti-CTFR1-FITC Mouse monoclonal mAb, Anti-CD 19 TR (Abcam) with Anti-CTFR1-FITC Mouse monoclonal mAb, Anti-CD 3 TR (Abcam) with Anti-CTFR1-FITC Mouse monoclonal mAb. Cells were then removed from the membrane using an Eppendorf Transferman micromipulator.

The following are materials that can be used for human cancer cell (See Example 10 for growing cancer cells) model testing: Anti-CTFR1-FITC Mouse monoclonal mAb (clone 444-1D12 Ekhart Ind.) at 2.58 mg/mL F to P 4:3 2.3 mL was used for cells to show negative, Anti-IDE (insulysin) rabbit pAb (calibiochem ST 1120) mixed with Anti-Rabbit TR goat polyclonal to mouse conjugated to TR (Abcam Ab 6716) was used for SKBR cell model testing, Anti TACE rabbit pAb (calibiochem PC491) mixed with Anti-Rabbit TR goat polyclonal to mouse conjugated to TR (Abcam Ab 6716) was also used for SKBR cell model testing, Muliplex Anti-IDE Anti IDE (insulysin) rabbit pAb (calibiochem ST1120) were used for cell models with Anti-Rabbit TR goat polyclonal to mouse conjugated to TR (Abcam) mixed with Anti IDE TACE (ADAM17) chicken pAb (R&D systems AF930) used for cell models with Anti Chicken Cy5 goat polyclonal to mouse conjugated with Cy5 (Abcam) used as multiplex assay for SKBR cell model testing.

The following are materials that can be used for blocking: Anti-Fc-Receptor antibody produced in rabbit (Abcam), Anti-CD32 antibody produced in rabbit, Anti-Fc-γ RII-a antibody produced in rabbit, Anti-Fc-γ-RIIa antibody produced in rabbit, Anti-FcRII-a antibody produced in rabbit, Anti-IgG Fc receptor II-a antibody produced in rabbit, Anti-Low affinity immunoglobulin γ Fc region receptor II-a precursor antibody produced in rabbit, Anti human conjugated ALP antibody (anti IgG ALP): The following are materials that was typically used for blocking was IgG gamma globulin human cohn fraction (G4368 Sigma Aldrich).

The following are general materials and tissues: Centrifuge tubes Nalgene 50 mL (#3110-9500) with tops.

Pancreas, liver, fat and quadriceps muscle was isolated from ZDF rats and were used for tissue sonication studies (used Sonicato Misonix Inc Sonicaton XL 2010 horn). A second set of tissue was isolated form ZDF rats including livers and lymph nodes. Pancreas, brain, liver, fat and quadriceps was muscle isolated from rabbits treated during polyclonal development and used for cryoslices (AML Laboratories) with separate slices obtained for left and right cerebral hemisphere and cerebellum Tissue was perfused with PBS at the time of collection. Tissue was embedded for frozen tissue slices with (OCT compound) and placed in a disposable base (cat no 22.363.544) in an ice bath and then frozen at −70° C. Rabbits 464, 465, and 466 were inoculated with keyhole limpet hemocyanin KLH CTF33 (SEQ ID NO: 1), and were responders, all making polyclonal antibodies against CIF. Whereas Rabbits 467,468, and 469 were inoculated with BSA CTF33 (SEQ ID NO: 1) and were non-responders, not making polyclonal antibodies against CTF. The rabbits were judged as responders or non responders using R1 CTF25 (SEQ ID NO: 11). Cell permeation solution was 0.2% Triton™ X100 in PBS. Cell Wash solution: Dilute 1 to 10 into PBS to make PBS/Tweet®-20 at 0.1%. DAPI: 4,6 Diamidino-2-phenylindole dihydrochloride MW 350.25 DAPI comes in 1 mg vial. Dissolve the DAPI in 1 ml TES to make a 1 mg/ml. The DAPI stock solution is stable for several months and repeated use if it is stored protected from light at −20° C. DAPI working solution is made by diluting the DAPI stock solution 1:10 in TES (100 µg/ml DAPI). Cancer cells: Breast cancer cells (ATCC) were cultured as described in example 10 and where grown to a concentration of ~200,000 cell/mL. Cells were diluted 10 ul into 1 mL to provide ~2000 cell/mL, or 2 cell/uL or 0.5 per HRP (HRP=0.2 uL). Microscopy was conducted by phase contrast and fluorescence microscopy with a Leica DM5000 microscope. The cover slips used were Fisher 12-548-6, Permafrost slides.

Filters used in microscopy are shown in Table 22.

TABLE 22

| Filters | Excitation filter | Emission filter | Fluorescence signal |
|---|---|---|---|
| A4 | 340-380 BP | 450-490 BP | DAPI |
| TX 2 | 540-580 BP | 610-680 BP | Texas red 592, 614 |
| L5 | 460-500 BP | 512-543 BP | FITC (ex 488, em 525 nm) |
| Y5 | | | |

Cancer and Blood Cell Staining

Cell samples were made by adding 100 ul of cell suspension to 1.0 mL of PBS with 5% IgG or BSA in wash buffer for 20,000 cell/mL (20 cell/uL or 5 per HRP (HRP=0.2 µL)) (this can also be done with whole blood). To assure cells were evenly distributed, the cells were vortexed. To 100 mL of testing standard 20 uL DAPI was added (diluted 1:10). 20 µL antibody was added. The cells were incubated for 15 minutes at 37° C. The cells were centrifuged down at 10 min @7500 rpm and the supernatant was decanted by tapping (~450 µL). The cells were washed with 1000 µL of PBS wash and vortexed. The cells were centrifuged down at 10 min @7500 rpm and the supernatant was decanted by tapping (~450 µL). 100 uL of PBS wash buffer was added for final the imaging solution. 5 uL was applied to the slide with a long cover slip of glass. Phase contrast and fluorescence microscopy was conducted with the Leica DM5000.

Rat Tissue Sample Staining for Cell Isolation

A tissue sample of 100 mg of tissue to 1 mL of PBS was made and sonicated at 240 Watts (40%) for 1 h until the cells were evenly distributed. The cells were not heated. Rather the cells were refrigerated to cool. 5 µL DAPI (diluted) was added to 100 uL of tissue sample. 10 uL of antibody (undiluted) was added to the sample and incubated for 15 minutes at RT. The sample was centrifuged down at 5 min @7500 rpm and the supernatant was decanted off by tapping (~450 µL). 100 µL of PBS wash buffer was added for the final image solution. 5 µL of the sample was applied to the slide with long cover slips of glass. Phase contrast and fluorescence microscopy was conducted with the Leica DM5000 microscope.

Rat Tissue Sample Staining for Tissue Fixation

Tissue samples were made with 100 mg of tissue to 1 mL of PBS. The sample was sonicated at 240 Watts (40%) for 15 min to 30 min until the tissues were thinner. The tissue was not heated. Rather, it was refrigerated to cool. The process tissue was added to microscope slides and the tissue areas were circled with hydrophobic pen to create an area for holding liquid. 100 µL of 5% formaldehyde in PBS was added to the circle area and the slide was incubated for 15 min at RT. The slides were next washed in permeabilization buffer (PBS/Triton™ X 100 at 0.2%) in a wash bath for 5-15 min. The sides were removed and the slides were allowed to drip dry and the Fe receptors on the tissues were then blocked by adding 50 µL of IgG at 5% in PBS (5 mg/mL) to the slide circled area and allowing the slide to stand for 15 min at RT. The slides were removed and washed in cell wash (PBS/Tween®-20 at 0.1%), by dipping the slides in a wash bath for 5 min. The slides were removed (might have to re-apply pen) and 50 µL of a stain was added to the circle area. The stain was made from (2.0 mL PBS, 100 uL DAPI (diluted to 0.01 mg/mL)) & 100 µL antibody (diluted to 0.1 mg/mL) and was added. The slide was incubated for 15 min at 37° C. and then removed. The slide was then washed in cell wash buffer (PBS/Tween®-20 at 0.1%), by dipping the slides into a wash bath for 5 min. Phase contrast and fluorescence microscopy were conducted with the Leica DM5000 microscope.

Rabbit Tissue Sample Staining for Tissue Fixation

Tissues slices for the microscope can be made according to any practice common to the art. The slice made were cyro slices at 8 um on perfused tissues and the tissues on the slides were circled with hydrophobic pen to create an area for holding liquid. 100 μL of 5% formaldehyde in PBS was added to the circle area and the slide was incubated for 15 min at RT. The slides were next washed in permeabilization buffer (PBS/Triton™ X 100 at 0.2%) in a wash bath for 5-15 min. The sides were removed and slides were allowed to drip dry and the Fc receptors on the tissues were then blocked by adding 50 μL of lei at 5% in PBS (5 mg/mL) to the slide circled area and allowing the slide to stand for 15 min at RT. The slides were removed and washed in cell wash (PBS/Tween®-20 at 0.1%), by dipping the slides in a wash bath for 5 min. The slides were removed (the pen may have to be reapplied) and 50 μL of a stain was added to the circle area. The stain was made from (2.0 mL PBS, 100 uL DAN (diluted to 0.01 mg/mL)) & 100 μL antibody (diluted to 0.1 mg/mL) was added. The slide was incubated for 15 min at 37° C. and then removed. The slide was then washed in cell wash buffer (PBS/Tween 20 at 0.1%) by dipping the slides into a wash bath for 5 min. Phase contrast and fluorescence microscopy were conducted with the Leica DM15000 microscope.

What is claimed:

1. A method for detecting Ig-C-terminal fragment of adiponectin receptor (Ig-CTF) in a biological sample, said method comprising:
   a. exposing a biological sample derived from a subject of a first species to a first antibody of a second species that preferentially binds the first species' Ig-CTF, said Ig-CTF comprising an immunoglobulin portion attached to a CTF peptide, said CTF peptide comprising the amino acid sequence of any one of SEQ ID NOs: 1 to 44, or an antigen-binding fragment of said first antibody, forming a mixture;
   b. exposing said mixture to a second antibody or an antigen-binding fragment of a third species that preferentially binds the first species' Ig; and
   c. detecting the Ig-CTF present in said sample.

2. A method of monitoring the level of Ig-C-terminal fragment of adiponectin receptor (Ig-CTF) in a subject of a first species, said method comprising:
   a. detecting Ig-CTF in a biological sample of the subject by using the method as claimed in claim 1;
   b. quantifying the amount of Ig-CTF present in said sample;
   c. comparing the amount of Ig-CTF present in the sample to either
      i. a known standard; or
      ii. the amount of IgG-CTF present in a biological sample obtained from the subject at an earlier point in time.

3. The method of claim 1 wherein said immunoglobulin portion comprises an immunoglobulin, and immunoglobulin heavy chain, an immunoglobulin light chain, or an immunoglobulin fragment.

4. The method of claim 1 wherein said immunoglobulin portion comprises SEQ ID NO: 45 or SEQ ID NO: 46.

5. The method of claim 1 wherein said second antibody or antigen-binding fragment is detectably labeled.

6. The method of claim 3 wherein said immunoglobulin is isotype IgG, IgA, IgM, IgD, or IgE.

7. The method of claim 1 wherein the first antibody or antigen-binding fragment is bound to a solid support.

* * * * *